United States Patent
Bloch et al.

(10) Patent No.: US 10,172,697 B2
(45) Date of Patent: Jan. 8, 2019

(54) POWERED TOOTHBRUSH

(71) Applicant: Colgate-Palmolive Company, New York, NY (US)

(72) Inventors: Brian Bloch, Hillsborough, NJ (US); Lars Ralf Rainer Lieberwirth, Glashuetten (DE)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/106,564

(22) PCT Filed: Dec. 17, 2014

(86) PCT No.: PCT/US2014/070923
§ 371 (c)(1),
(2) Date: Jun. 20, 2016

(87) PCT Pub. No.: WO2015/095373
PCT Pub. Date: Jun. 25, 2015

(65) Prior Publication Data
US 2016/0338808 A1 Nov. 24, 2016

(30) Foreign Application Priority Data

Dec. 19, 2013 (CN) .......................... 2013 1 0701780

(51) Int. Cl.
*A46B 15/00* (2006.01)
*A61C 17/22* (2006.01)
(Continued)

(52) U.S. Cl.
CPC .......... *A61C 17/221* (2013.01); *A46B 5/0095* (2013.01); *A46B 9/04* (2013.01);
(Continued)

(58) Field of Classification Search
CPC . A46B 15/0006; A61C 17/221; A61C 17/225; G06F 3/044
See application file for complete search history.

(56) References Cited

U.S. PATENT DOCUMENTS 8,898,843 B2 12/2014 Okazaki
9,525,417 B2 12/2016 Inada et al.
(Continued)

FOREIGN PATENT DOCUMENTS

EP 1058513 12/2000
EP 1624399 2/2006
(Continued)

OTHER PUBLICATIONS

Corresponding Search Report and Written Opinion for PCT/US2014/070923 dated Feb. 24, 2015.

*Primary Examiner* — Randall Chin

(57) ABSTRACT

A powered toothbrush apparatus with capacitive touch control, which includes a head portion having an oscillating tuft block driven by a motor, a handle portion, and an elastically deformable capacitive touch control panel mounted in the handle portion. In one embodiment, the control panel includes movable sensor targets each paired with a corresponding capacitance sensor electrically connected to a programmable microprocessor. Applying finger pressure on the control panel adjacent a sensor target operates to change the capacitance of the respective sensor target-sensor pair. The microprocessor detects the change in capacitance, which may be used to control the motor speed for changing the oscillation rate of the tuft block. In one embodiment, a linear array of sensor targets-sensors is provided which is activated by a sliding finger or thumb motion across the array. A related operating method is disclosed.

12 Claims, 19 Drawing Sheets

(51) Int. Cl.
  *G06F 3/044* (2006.01)
  *A46B 5/00* (2006.01)
  *A46B 9/04* (2006.01)
  *A61C 17/34* (2006.01)
  *B08B 1/00* (2006.01)
  *A61C 17/32* (2006.01)

(52) U.S. Cl.
  CPC ........ *A46B 15/0006* (2013.01); *A61C 17/225* (2013.01); *A61C 17/3445* (2013.01); *B08B 1/002* (2013.01); *G06F 3/044* (2013.01); *A61C 17/32* (2013.01)

(56) References Cited

U.S. PATENT DOCUMENTS

| | | |
|---|---|---|
| 2009/0064430 A1 | 3/2009 | Jimenez |
| 2013/0177863 A1 | 7/2013 | Shreve |
| 2014/0123414 A1 | 5/2014 | Okazaki |
| 2014/0250612 A1* | 9/2014 | Curry .................. A61C 17/221 15/22.1 |

FOREIGN PATENT DOCUMENTS

| | | |
|---|---|---|
| JP | 2009273621 | 11/2009 |
| WO | WO0100003 | 1/2001 |
| WO | WO2012042493 | 4/2012 |

* cited by examiner

POWERED TOOTHBRUSH

CROSS-REFERENCE TO RELATED PATENT APPLICATIONS

The present application is a U.S. national stage application under 35 U.S.C. § 371 of PCT Application No. PCT/US2014/070923, filed Dec. 17, 2014, claims priority to Chinese Patent Application No. 201310701780.8, filed on Dec. 19, 2013, the entireties of which are incorporated herein by reference.

BACKGROUND

Powered toothbrushes are known having various movable tuft blocks on which tooth cleaning elements are mounted. The movable tuft blocks are driven by an electric motor configured to oscillate the tuft block in a predetermined brushing motion. Various types of approaches including mechanical or electronic switches may be used to control motor speed or other functions of the tooth brush. Improvements in such powered toothbrush controls are desirable.

BRIEF SUMMARY

According to one embodiment, a powered toothbrush apparatus with capacitive touch control includes a motor, a handle portion, a capacitive touch control panel in the handle portion, and a plurality of capacitance sensors operably associated with the control panel. Each of the plurality of capacitance sensors has a capacitance value that is changed by a user touching a specific location of the control panel, thereby activating the capacitance sensor. A microprocessor in the handle portion is electrically connected to the plurality of capacitance sensors and the motor. The microprocessor configured to: (1) detect changes in the capacitance values of the plurality of capacitance sensors; (2) measure time intervals occurring between changes in the capacitance values of adjacent ones of the plurality of capacitance sensors; and (3) change speed of the motor upon determining that each of the plurality of capacitance sensors has been activated in a predetermined sequential order and that each of the measured time intervals is at or below a maximum predetermined time interval. The toothbrush may further include a head portion including an oscillating tuft block driven by the motor, the tuft block including a plurality of tooth cleaning elements. In one embodiment, the motor may be mounted in the handle portion. In other embodiments, the motor may be mounted in the head portion.

According to another embodiment, a powered toothbrush apparatus with capacitive touch control includes a motor, a handle portion coupled to the head portion, a capacitive touch control panel mounted in the handle portion, the control panel being elastically deformable in response to the application of inward directed finger pressure by a user, and a plurality of capacitance sensors mounted in the handle portion, each sensor paired with a corresponding movable conductive sensor target disposed on the deformable control panel above the sensor, each sensor target being movable towards its paired sensor in response to a user applying finger pressure to the control panel, wherein each sensor and sensor target pair has a capacitance that is changed by applying finger pressure on the control panel adjacent to the sensor target. A microprocessor is mounted in the handle portion and electrically connected to the sensors and the motor. The microprocessor being configured to: detect changes in the capacitance values of the plurality of capacitance sensors; measure time intervals occurring between changes in the capacitance values of adjacent ones of the plurality of capacitance sensors; and change speed of the motor upon determining that each of the plurality of capacitance sensors has been activated in a predetermined sequential order and that each of the measured time intervals is at or below a maximum predetermined time interval.

A method for controlling a powered toothbrush apparatus speed is provided. The method includes: providing a powered toothbrush including a handle portion, a motor, an elastically deformable capacitive touch control panel mounted in the handle portion and including a plurality of conductive sensor targets movable by deforming the control panel, and a linear array of capacitance sensors each paired with one of the sensor targets, each sensor having a capacitance that is changed by a pressing action on the control panel adjacent a sensor target; a user applying a pressing and sliding motion with a finger or thumb linearly across the control panel over the plurality of sensor targets in sequential order; the user deforming the control panel inwards over each sensor by the pressing and sliding motion to activate each of the sensors in sequential order; a microprocessor detecting a change in capacitance in each activated sensor; and the microprocessor changing speed of the motor in response to the detected changes in capacitance of each sensor.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

Figure 1:
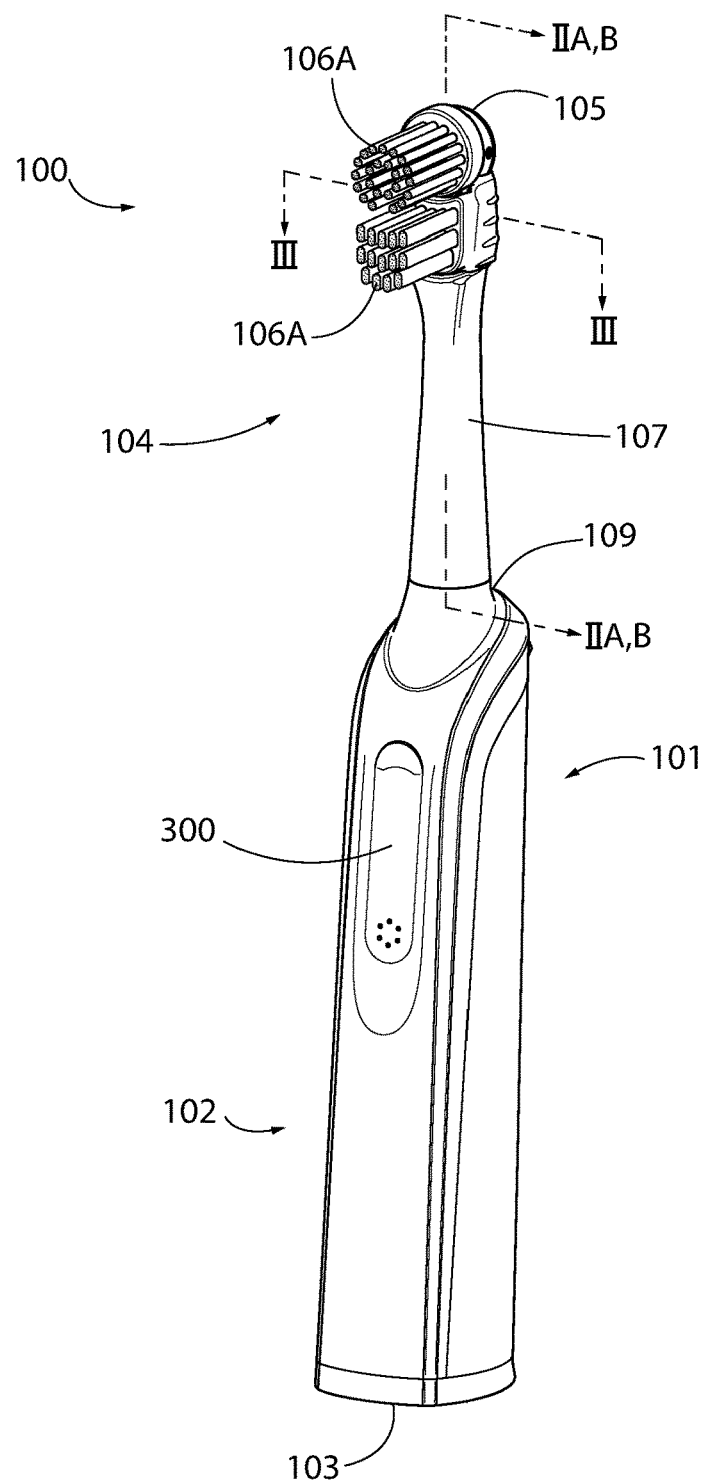
FIG. 1 is a perspective view of a powered toothbrush according to the present disclosure.

All drawings are schematic and not necessarily to scale.

DETAILED DESCRIPTION

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

FIG. 1 depicts a non-limiting exemplary embodiment of an oral care implement in the form of an electric-powered toothbrush 100. Toothbrush 100 includes an elongated body 101 including a handle portion 102 defining a proximal end 103, a head portion 104 defining a distal end 105, and a longitudinal axis LA extending between the proximal and distal ends. Head portion 104 supports a plurality of tooth cleaning elements 106. In one embodiment, head portion 104 may be detachably mounted to handle portion 102 to form a replaceable unit or refill thereby allowing a user to replenish the head portion after the tooth cleaning elements 106 have been worn and/or to change the type of tooth cleaning elements. Accordingly, a separable joint is formed between the head and handle portions 104, 102 of toothbrush 100 in such embodiments.

Handle portion 102 and head portion 104 of toothbrush 100 may be constructed of a material or combination of materials having suitable rigidity for grasping/handling the toothbrush and supporting the tooth cleaning elements 106, respectively. Suitable exemplary materials that may be used include, without limitation, hard plastics, such as polyethylene, polypropylene (PP), polyamide, polyester, cellulosics, SAN, acrylic, ABS and other thermoplastics suitable for toothbrush manufacture. The handle portion 102 and head portion 104 may be made of the same or different materials in various embodiments.

Figure 7:
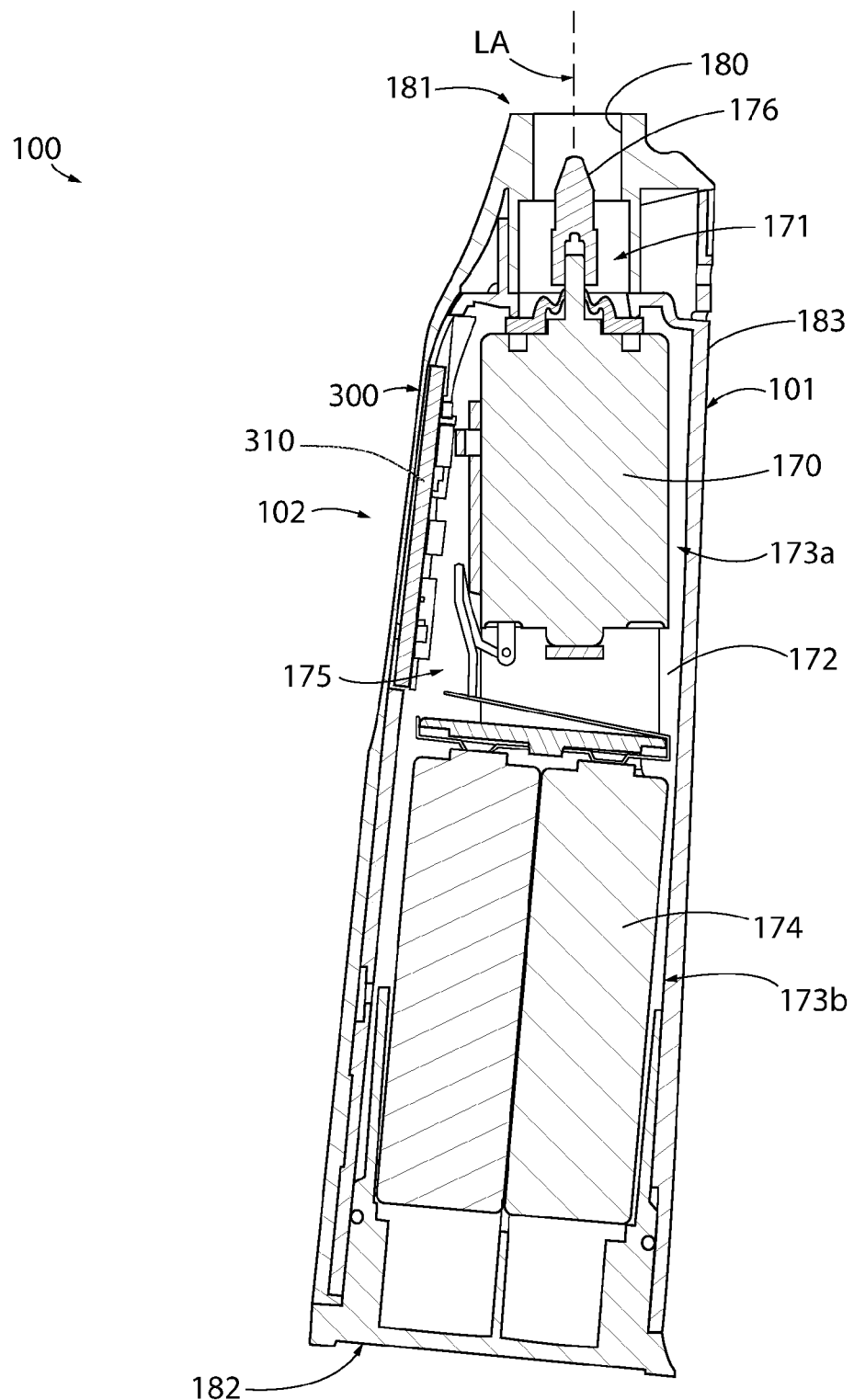
FIG. 7 is a side cross sectional view of the handle portion of toothbrush of FIG. 1.

FIG. 7 depicts a cross sectional side elevation view of toothbrush handle portion 102 alone. Referring to FIGS. 1 and 7, handle portion 102 includes a top wall 181, bottom wall 182, and side walls 183 extending between the top and bottom. Top wall 181 may include a socket 180 configured for receiving a complementary configured stem 184 on head portion 104 (see, e.g. FIGS. 2A and 2B) for mounting the head portion to the handle portion. In one embodiment, socket 180 and stem 184 may have circular cross sections; however, any suitable cross sectional shape including rectilinear and polygonal shapes may be provided (e.g. square, hexagonal, triangular, etc.).

Referring to FIGS. 1 and 7, handle portion 102 further includes an internal chamber 172 which defines a motor compartment 173a for supporting DC electric motor 170 and a battery compartment 173b configured for holding one or more batteries 174. Motor and battery compartments 173a, 173b may be contiguous or isolated from each other in chamber 172. Batteries 174 may be of any type including replaceable cells and/or rechargeable cells which are electrically connected to motor 170 via electrical connectors 175 which may include conductive contacts, wires, etc. Motor 170 includes a revolving rotor 171 have an end drive coupling 176 configured for detachable coupling to and driving a drive shaft 130 disposed in toothbrush head portion 104 (see, e.g. FIGS. 2A and 2B). Rotation of the motor rotor 171 in turn rotates the drive shaft 130 about its central axis CA. An operating panel 300 is provided which is electrically connected to motor 170 and includes switches or other type actuators for controlling on/off operation and/or speed of the motor.

Figure 2A:
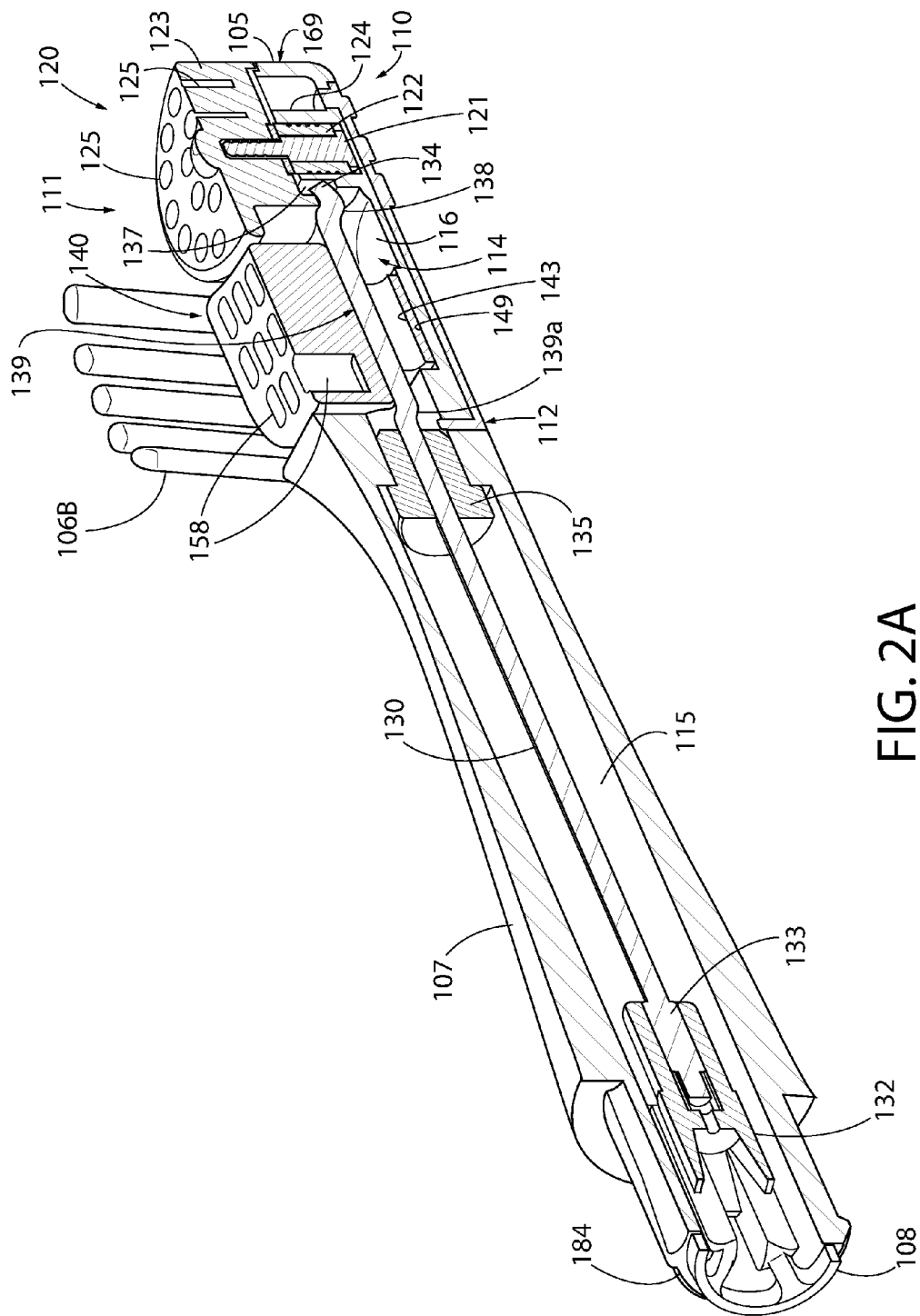
FIG. 2A is cross sectional perspective view of the head portion of the toothbrush taken along line IIA-IIA in FIG. 1.
Figure 2B:
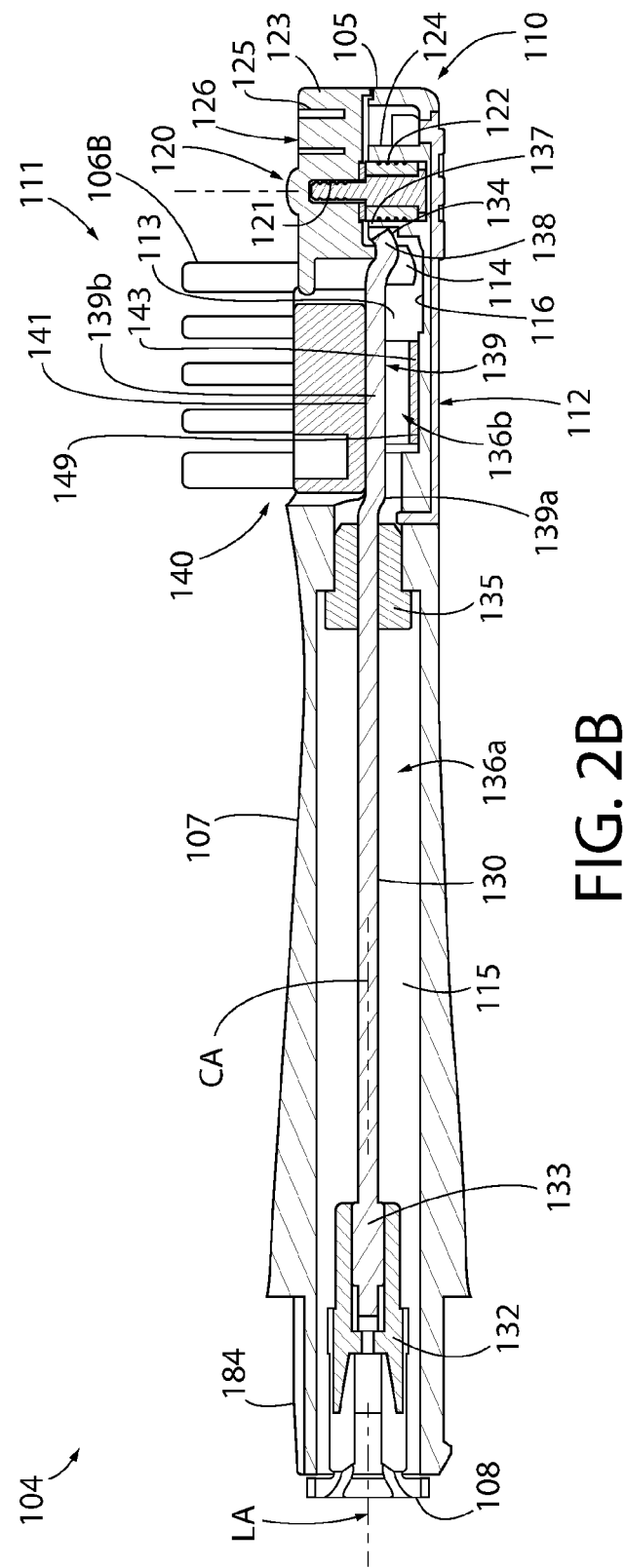
FIG. 2B is a side cross sectional view of the head portion of the toothbrush taken along line IIB-IIB in FIG. 1.
Figure 3:
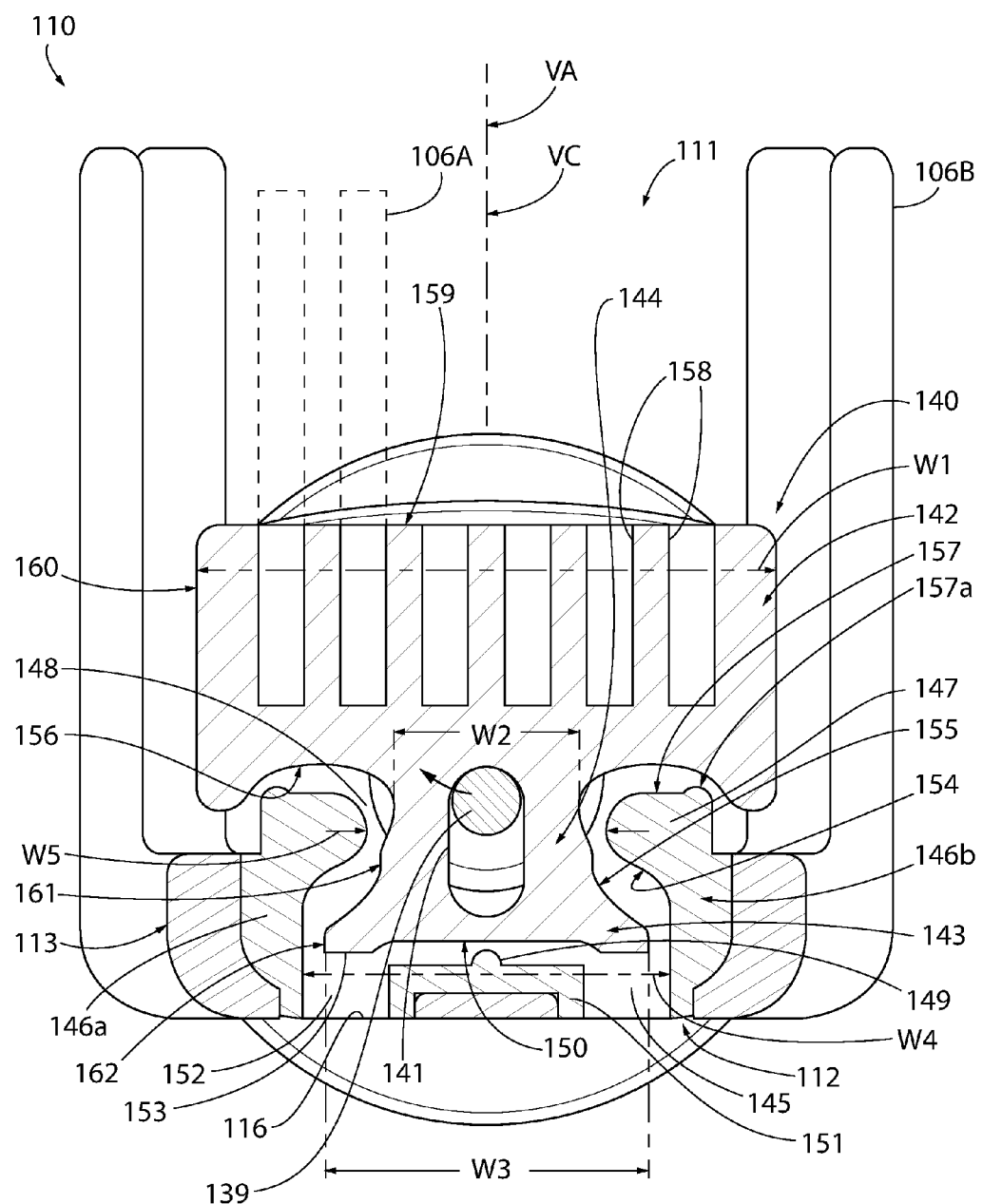
FIG. 3 is a transverse cross sectional view of a movable tuft block taken along line III-III in FIG. 1.

FIGS. 2A and 2B depict cross sectional perspective and side elevation views of toothbrush head portion 104 alone. FIG. 3 depicts a transverse cross section taken along line III-III in FIG. 1 through one of the tuft blocks 140. In one configuration, head portion 104 includes a head 110 and an elongated neck 107 connected to the head. Neck 107 defines an open proximal end 108 of head portion 104 lying along longitudinal axis LA opposite distal end 105 of toothbrush 100 which is defined by head 110. Proximal end 108 is configured for detachable mounting to a distal end 109 of the handle portion 102.

Toothbrush head 110 comprises a front side 111, an opposing rear wall 112, and opposing lateral side walls 113 extending around the periphery of the head. The rear and side walls 112, 113 define an internal cavity 114 which is open through the front side 111 of the head 110 and configured to receive tuft blocks 120, 140, as further described herein. Cavity 114 may therefore have a closed bottom surface 116 formed by rear wall 112 of head 110 and open top 117 facing and extending through the front side 111 of the head.

The rear walls 112 and lateral side walls 113 of head 110 can take on a wide variety of shapes and contours, none of which are limiting of the present invention. For example, these walls can be planar, contoured, or combinations thereof. Head 110 may be laterally widened in a direction transverse to longitudinal axis LA in contrast to neck 107 in some embodiments for supporting a variety of tooth cleaning elements 106.

In the exemplary embodiment, the neck 107 and head 110 of head portion 104 may be integrally formed as a single unitary structure using a molding, milling, machining and/or other suitable fabrication processes. However, in other embodiments the neck 107 and head 110 may be formed as separate components which are then connected at a later stage of the manufacturing process by any suitable technique known in the art, including without limitation thermal or ultrasonic welding, a tight-fit assembly, a coupling sleeve, threaded engagement, adhesion, or fasteners. Whether the head 110 and the handle 120 are of a unitary or multi-piece construction (including connection techniques) is not limiting of the present invention, unless specifically claimed.

Head 110 of toothbrush 100 is configured and structured to support a plurality and variety of different tooth cleaning elements 106 from the front side 111. As used herein, the term "tooth cleaning elements" is used in a broad generic sense to refer to any structure whatsoever that can be used to clean, polish, scrape, or wipe the teeth and/or soft oral tissue (e.g. tongue, cheek, gums, etc.) through relative surface contact. Examples of tooth cleaning elements that may be used include, without limitation, bristle tufts, filament bristles, fiber bristles, nylon bristles, spiral bristles, rubber bristles, elastomeric protrusions, flexible polymer protrusions, combinations thereof and/or structures containing such materials or combinations. Suitable elastomeric materials include any biocompatible resilient materials suitable for uses in an oral hygiene apparatus. The tooth cleaning elements 106 may be attached to head 110 by any suitable method used in the art. For example, without limitation, in-mold tufting (IFT) or anchor free tufting (AFT) could be used to mount the cleaning elements. Accordingly, invention is not limited by the types of tooth cleaning elements 106 provided or method of anchoring those elements to head 110 of head portion 104.

In one non-limiting embodiment, neck 107 may be generally tubular shaped having a circular and annular transverse cross section which may vary in diameter along the length of the neck in some configurations. Numerous other variations in the shape and configuration of neck 107 are possible. Neck 107 defines a longitudinally extending internal passageway 115 which extends through the neck from open proximal end 108 of head portion 104 into open cavity 114 formed in the head 110. Passageway 115 therefore communicates with cavity 114.

Referring to FIGS. 2A-B and 3, a drive shaft 130 is rotatably disposed inside head portion 104. Drive shaft 130 extends through internal passageway 115 from a point near proximal end 108 towards distal end 105 along longitudinal axis LA. In one embodiment, drive shaft 130 has a driven proximal section 136a disposed in neck 107 which may be substantially straight in one non-limiting embodiment and a working distal section 136b projecting into open cavity 114 of head 110 that is configured for operating movable tuft blocks 120, 140, as further described herein. Proximal end 133 of drive shaft 130 includes an adapter coupling 132 configured for detachably engaging drive coupling 176 of motor 170 disposed in handle portion 102 (see FIG. 7), thereby coupling the drive shaft to the motor. Rotation of the motor rotor 171 in turn rotates the drive shaft 130 about its central axis CA. In various embodiments, central axis CA may be concentrically aligned with or parallel to longitudinal axis LA. A bearing 135 may be disposed between the proximal and distal sections 136a, 136b of the drive shaft 130 near the conjuncture between the neck 107 and head 110 for supporting the drive shaft 130. This helps support the working distal section 136b against transverse or shear forces imposed on the drive shaft 130 when a user is brushing and presses the tooth cleaning elements 106A against their oral surfaces.

Toothbrush head 110 may include one or more powered movable tuft blocks 120 and 140 which are engaged by distal section 136b of drive shaft 130. Tuft blocks 120, 140 are each configured for mounting a plurality of moving tooth cleaning elements 106A thereto, as further described herein. Each shaft-driven tuft block 120, 140 may include tooth cleaning elements 106A in the form of bristles and/or elastomeric cleaning elements. Head 110 may further include non-motor-driven fixed or stationary tooth cleaning elements 106B in addition to any movable tuft blocks provided. The stationary tooth cleaning elements 106B may similarly include bristles and/or elastomeric cleaning elements. As used herein, the terms "movable" tuft blocks and "moving" tooth cleaning elements refers to tuft blocks and tooth cleaning elements which have motion produced via operation of a power drive (e.g. motor) without contact with a user's oral surfaces (e.g. teeth, gums, etc.) during brushing to impart movement. The terms "fixed" or "stationary" tooth cleaning elements refers to elements that are static when not in contact with a user's oral surfaces and move primarily only as a result of the tooth brushing action.

Referring to FIGS. 2 and 3, tuft block 120 may be a distal-most tuft block disposed near distal end 105 and end wall 169 of toothbrush head 110. In one embodiment, tuft block 120 may be an oscillating type tuft block as described U.S. Pat. No. 5,625,916, which is incorporated herein by reference in its entirety. Tuft block 120 is rotationally and arcuately movable back and forth in reversible directions through a limited arcuate path around a center support spindle 121 which is oriented transversely to longitudinal axis LA and defines an axis of rotation. Spindle 121 may be mounted in and supported by a suitable bearing 122 disposed in receptacle 124 formed inside cavity 114 to provide smooth rotational movement of the spindle. In some embodiments, a majority of tuft block 120 may be generally positioned in open cavity 114 formed in head 110.

In one embodiment, tuft block 120 is actuated and operated by a first angular offset segment formed by a curved or eccentric distal end 134 of drive shaft 130 which defines a first eccentric cam 138. Cam 138 may have a generally hooked configuration which includes a double bend having a first portion bent outwards away from the central axis CA of drive shaft 130 and a second portion bent back inwards towards the central axis CA. Cam 138 engages an operating slot 137 formed in a side of tuft block 120. Rotation of drive shaft 130 through 360 degrees oscillates or pivots tuft block 120 back and forth transversely to longitudinal axis LA of toothbrush 100 through an arcuate path of motion around spindle 121. In one representative but non-limiting example, the arcuate path of motion may be between about and including 10-90 degrees, and more particularly 20-30 degrees in some embodiments.

As shown in FIGS. 2A and 2B, tuft block 120 includes a plurality of openings 125 formed in an outward facing top surface 126 of an upper bristle holding portion 123 which are configured for inserting and mounting bristle tufts and/or elastomeric cleaning elements through the openings. Openings 125 may be of any suitable shape (in top plan view). Tuft block 120 may have any suitable configuration. In one non-limiting embodiment, tuft block 120 may have a circular shape in top plan view. Numerous other variations in shape are possible.

Referring initially to FIGS. 2A-B and 3, tuft block 140 in one non-limiting exemplary embodiment may be generally T-shaped or mushroom-shaped in transverse cross section. Toothbrush 140 includes an upper bristle holding portion 142, a lower base portion 143, and a narrowed reduced width intermediate portion 144 between portions 142 and 143. Bristle holding portion 142 has a vertical height sufficient for mounting bristles and/or elastomeric tooth cleaning members. A plurality of openings 158 formed in an outward facing top surface 159 of an upper bristle holding portion 142 are configured for inserting and mounting bristle tufts and/or elastomeric cleaning elements such as tooth cleaning elements 106A (illustrated in dashed lines) through the openings. Openings 158 may be any suitable shape (in top plan view). Top surface 159 extends transversely to longitudinal axis LA between the opposing lateral sides 160. In one embodiment, top surface 159 may be substantially flat; however, arcuately curved or undulating profiles may also be used. Tuft block 140 may be longitudinally elongated having a larger axial length (measured parallel to longitudinal axis LA) than lateral width measured between the lateral sides 160.

In one embodiment, bristle holding portion 142 has a width W1 which may be wider than width W2 of the intermediate portion 144 (measured at its narrowest point between lateral sides 161), and in some embodiments width W1 may be wider than width W3 of base portion 143 between lateral sides 162. Width W2 of intermediate portion 144 may be smaller than both widths W1 and W3 of bristle holding and base portions 142 and 143, respectively. This captures or traps the base portion 143 in a receptacle 145 formed within a portion of cavity 114 in toothbrush head 110 to prevent the tuft block 140 from being transversely extracted from the cavity through the front side 111 of the head, as further described herein.

Receptacle 145 may be formed and defined by opposing lateral walls 146a, 146b positioned in cavity 114 (see, e.g. FIG. 3). Walls 146a, 146b may be separate structures mounted inside the cavity 114 or may be formed by integral interior portions of lateral side walls 113 of the toothbrush head 110. In one embodiment, walls 146a, 146b may further define a pair of inward projecting operating flanges 147 which each extend towards longitudinal axis LA. Flanges 147 are spaced laterally/transversely apart to form a reduced width entrance 148 to receptacle 145 from front side 111 of toothbrush head 110. Entrance 148 has a lateral width W2 which is less than width W4 of receptacle 145. The free ends of flanges 147 may each have convexly curved or rounded surfaces to smoothly and slidingly engage tuft block 140, as further described herein. Portions of walls 146a, 146b below flanges 147 may be substantially vertical in one embodiment. The transition or shoulders 154 formed between flanges 147 and walls 146a, 146b may be concavely rounded to avoid sharp corners and provide a gradually contoured sliding surface configured to abuttingly and slidingly contact outwardly flared leg extensions 153 on base portion 143 of tuft block 140 for smooth movement.

A bottom portion of the receptacle 145 may further include an upwardly extending protuberance 149 formed above and generally proximate to and adjacent rear wall 112 of toothbrush head 110. Referring to FIGS. 2A-B and 3, protuberance 149 defines a pivot configured to engage a bottom surface 150 formed on base portion 143 of tuft block 140. In one embodiment, protuberance 149 may be generally shaped as a longitudinally extending ridge formed inside receptacle 145. In that configuration, protuberance 149 may have an axial length measured along the longitudinal axis LA which is substantially coextensive with the axial length of base portion 143 of tuft block 140 to restrict movement of the tuft block to a side-to-side lateral rocking motion and minimize rocking in a back and forth direction (i.e. proximal to distal) along the longitudinal axis LA. A ridge-shaped protuberance 149 may have a continuous or interrupted length and structure. Other variations in the shape and configuration of protuberance 149 however are possible. For example, in another possible embodiment, protuberance 149 may have a semi-spherical or half round shape (e.g. dimple or nub) with a limited axial length substantially less than the axial length of tuft block base portion 143.

In one embodiment, protuberance 149 may be formed on a raised pedestal 151 extending upwards from the bottom surface 116 of the cavity 114 within the confines of receptacle 145. Pedestal 151 may be a separate structure mounted inside the receptacle 145 or may be formed by integral interior portion of rear wall 112 of the toothbrush head 110. The pedestal 151 forms two pockets 152 on either lateral side for receiving laterally and outwardly flared leg extensions 153 on base portion 143 of tuft block 140 during movement of the tuft block. Leg extensions 153 extend laterally farther than intermediate portion 144 of tuft block 140.

Referring to FIG. 3, intermediate portion 144 may have generally concave curved lateral surfaces 155 for abuttingly and slidingly engaging the rounded flanges 147 formed in toothbrush head 110. This ensures smooth and unbinding motion as the tuft block 140 moves through its various positions, as further described herein. Similarly, the underside of upper bristle holding portion 142 of tuft block 140 may include concavely rounded bottom surfaces 156 contoured for smoothly engaging the top surface 157 of rounded flanges 147 formed in toothbrush head 110. The top surface may be configured to include raised longitudinally extending rails 157a to facilitate smooth non-binding contact with the underside surfaces 156 of the tuft block upper bristle holding portion 142.

In one embodiment, tuft block 140 is mounted on and actuated by a second angular offset segment formed by a curved or eccentric portion of drive shaft 130 which defines a second eccentric cam 139. Referring to FIGS. 2A, 2B, and 3, cam 139 is disposed between distal end 134 and proximal end 133 of drive shaft 130. In various embodiments, cam 139 may include at least one bend 139a as shown with an adjoining straight segment 139b having an axis which is transversely offset from and parallel to central axis CA of drive shaft 130. Cam 139 is configured and arranged to engage a vertically oriented and elongated operating slot 141 in tuft block 140 for moving the tuft block in a plurality of directions transverse to longitudinal axis LA of toothbrush 100 as the drive shaft 130 rotates. In one alternative embodiment, two bends 139a may be provided with offset straight segment 139b disposed therebetween.

It should be noted that in the embodiment shown in FIG. 3, none of the peripheral edges or sides of tuft block 140 are attached or coupled to toothbrush head 110 so that the tuft block is freely movable to translate in position vertically, laterally, and angularly (i.e. tilting) transverse to longitudinal axis LA when driven by drive shaft cam 139. This allows tuft block 140 to simulate a Bass brushing technique preferred by many oral care professionals. The sole point of coupling in the present embodiment between tuft block 140 and the toothbrush head portion 104 is via cam 139 engaging slot 141 formed in intermediate portion 144 of the tuft block. The range of vertical, lateral, and angular motion may be restricted by design via engagement between base and intermediate portions 143, 144 of tuft block 140 and flanges 147 formed in receptacle 145 of toothbrush head 110, as further described herein.

The powered operation and brushing motion created by tuft block 140 will now be described in greater detail. FIGS.

4A-I illustrate sequential "still" images showing various positions of tuft block 140 occurring during completion of a full oscillation cycle of tuft block 140 when driven by motorized drive shaft 130. It will be appreciated that these positions shown occur rapidly in a fraction of a second as part of a continuous cyclical motion produced by the rotating drive shaft and eccentric cam 139 formed thereon. In this embodiment, the oscillation cycle of brushing motion replicates the Bass brushing technique.

For clarity, all elements of tuft block 140 have not been labeled in FIGS. 4A-I to better show the positions of the tuft block in motion and interaction with various parts of the toothbrush head portion. Accordingly, reference should also be made to FIG. 3 recognizing that similarly drawn parts without labels are the same in FIGS. 4A-I as in FIG. 3.

In one exemplary embodiment, a method for moving a tuft block 140 of a powered toothbrush 100 through an oscillation cycle includes first providing a powered toothbrush 100 having a movable head portion 104. In FIGS. 4A-I, the drive shaft 130 rotates in a clockwise direction and eccentric cam 139 rotates clockwise about the drive shaft to drive tuft block 140 through the oscillation cycle. The vertical axis VA shown in FIGS. 3 and 4A-I will provide a plane of reference useful in describing the orientation of tuft block 140 during various parts of the oscillation cycle. The drive shaft 130 defines a longitudinally oriented or horizontal axis of rotation extending along longitudinal axis LA thereby providing another point of reference for describing the motion of tuft block 140. Because the top (upper bristle holding portion 142), bottom (base portion 143), and lateral sides of tuft block 140 (i.e. lateral sides 160, 161, and 162) are not physically attached to the lateral side walls 113 or bottom wall 112 of toothbrush head 110 in which the tuft block is mounted, this free floating arrangement of tuft block 140 advantageously provides three degrees of motion not being constrained to simply vertical movement or pivoting movement about a fixed pivot axis alone. Accordingly, tuft block 140 is free to move angularly (i.e. rock or tilt), vertically, and laterally (horizontally) allowing an oscillation cycle of motion to be provided by a powered toothbrush that beneficially replicates compound brushing motions (e.g. Bass motion) normally achieved by manual brushing techniques.

Figure 4A:
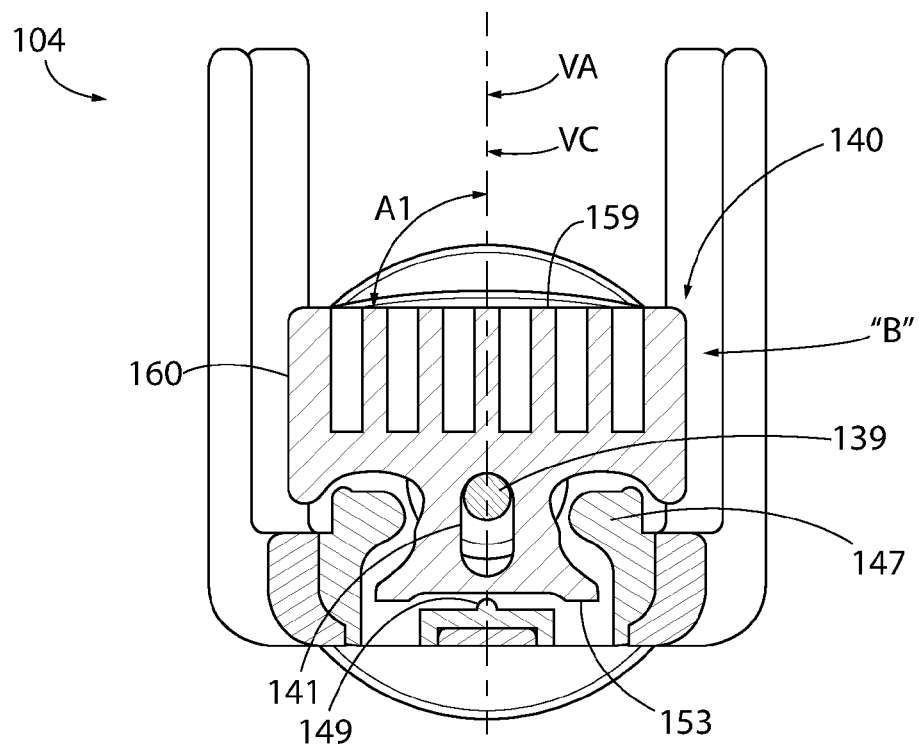
FIGS. 4A-I show sequential transverse cross sectional views of the movable tuft block of FIG. 3 during an oscillation cycle of a motor-driven brushing action.
Figure 4B:
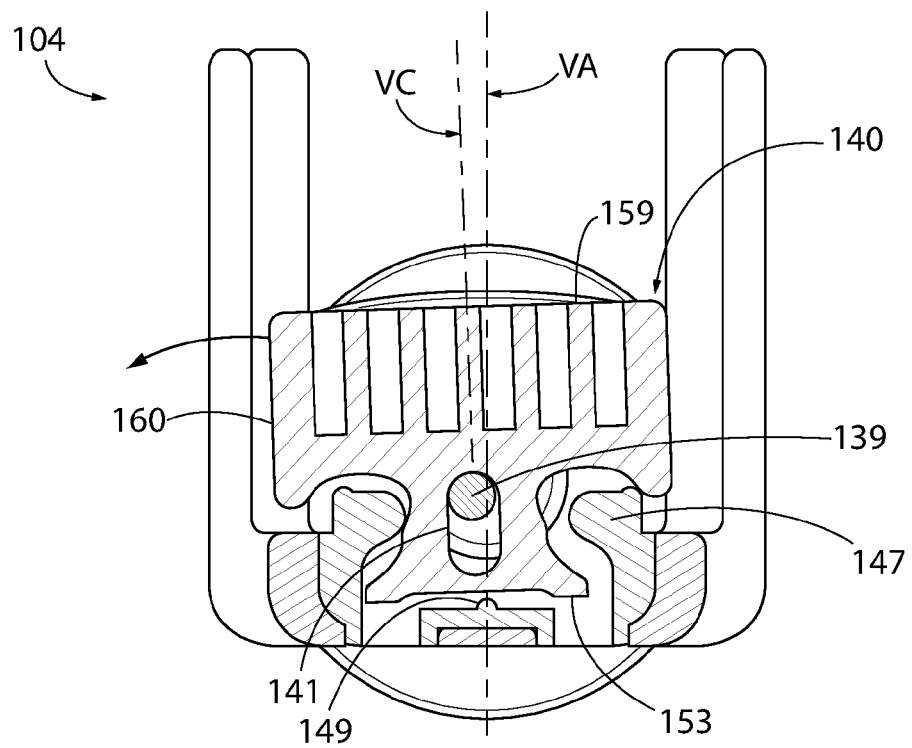
Figure 4C:
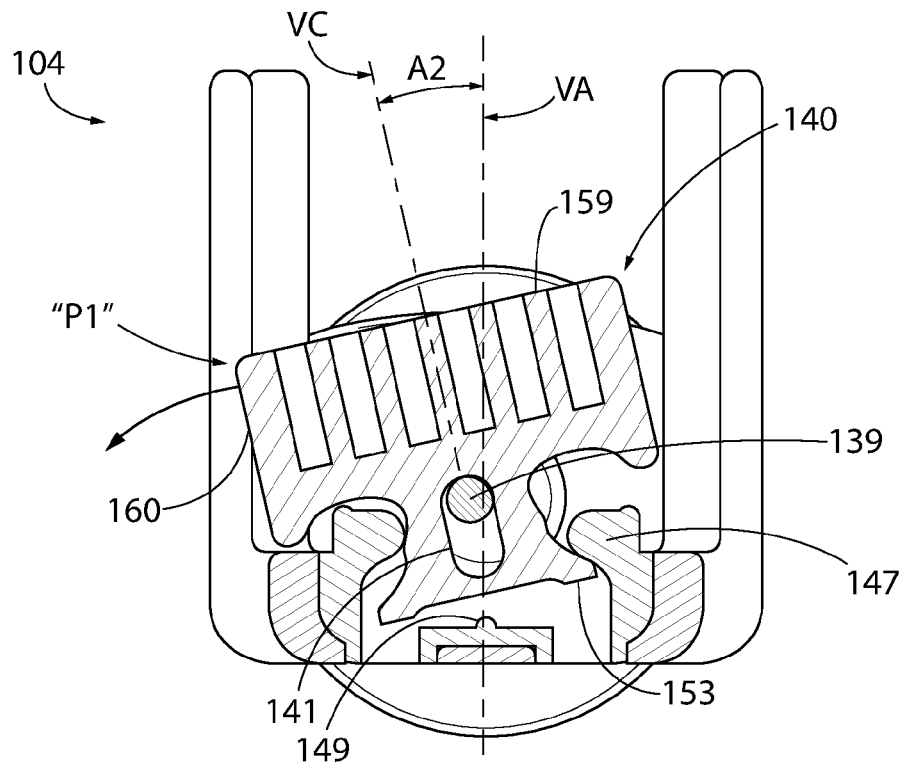
Figure 4D:
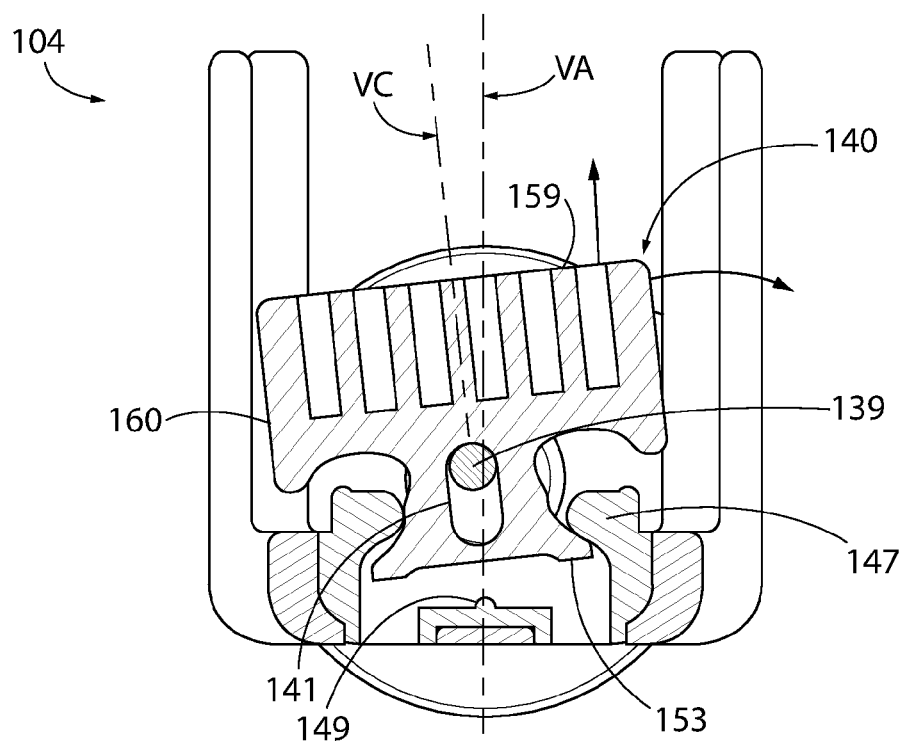
Figure 4E:
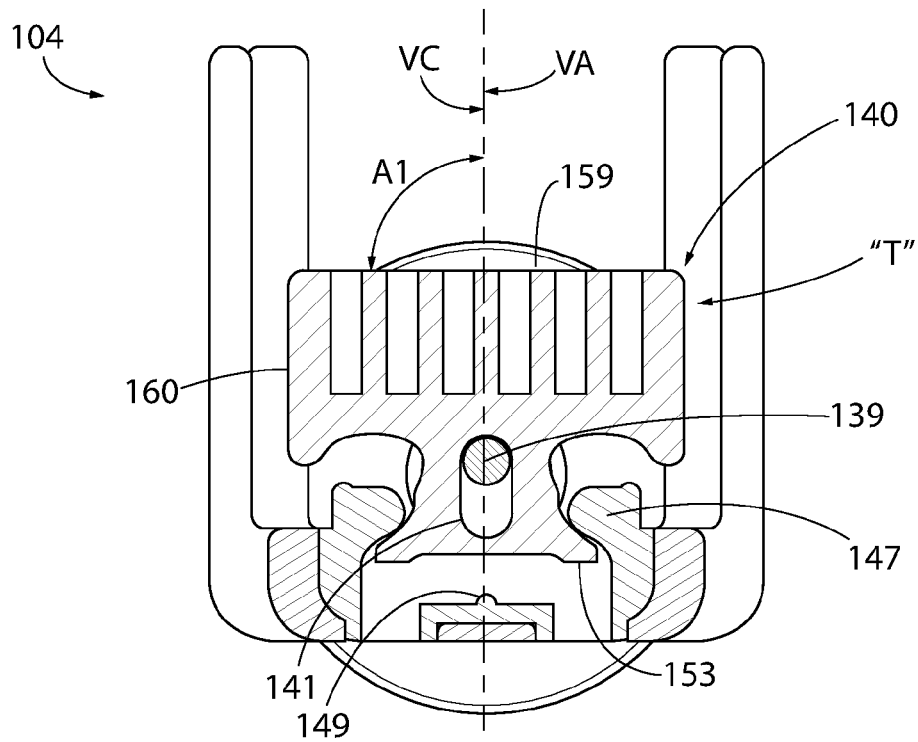

Tuft block 140 is movable in an oscillation cycle through a lowermost bottom vertical position "B" shown in FIG. 4A and an uppermost top vertical position "T" shown in FIG. 4E via a combination of vertical raising/lowering, lateral, and tilting motions, as further described herein.

The oscillation cycle will be described for convenience without limitation with arbitrarily locating tuft block 140 in a starting position at the bottom vertical position "B" shown in FIG. 4A. Tuft block 140 is in an upright orientation wherein top surface 159 of the tuft block faces upwards and is oriented at an angle A1 of approximately 90 degrees (i.e. perpendicular) to vertical axis VA of head portion 104. Accordingly, tuft block 140 is not substantially tilted or angled to one side or the other of vertical axis VA such that the lateral sides 160 of the upper bristle holding portion 142 are each spaced approximately equidistant from and parallel to the vertical axis.

In the starting bottom vertical position "B", the bottom surface 156 of upper bristle holding portion 142 is in contact with or located proximate to top surface 157 of opposing flanges 147 (see FIG. 4A). Bottom surface 150 of tuft block base portion 143 is vertically spaced distally to flanges 147 and proximately to protuberance 149. In some embodiments, the bottom surface 150 may contact and rest on protuberance 149. In this upright orientation of tuft block 140, small lateral gaps may be present in some arrangements between reduced width intermediate portion 144 of the tuft block and the free ends of flanges 147 on the toothbrush head portion 104.

To further describe orientations of tuft block 140 with respect to vertical axis VA during an oscillation cycle, tuft block 140 may be considered to define a vertical centerline VC extending vertically through the tuft block and oriented perpendicular to top surface 159 of the upper bristle holding portion 142 (see, e.g. FIG. 4B). Vertical centerline VC is further defined as extending through drive shaft 130 and spaced equidistant between the lateral sides 160 of upper bristle holding portion 142. In the bottom vertical position "B" of tuft block 140 shown in FIG. 4A, vertical centerline VC is axially aligned and coincides with vertical axis VA of toothbrush head portion 104. It will be noted that vertical axis VA associated with toothbrush head portion 104 provides a fixed or stationary point of reference on toothbrush head portion 104 while vertical centerline VC provides an angularly movable point of reference depending on the various tilted or canted orientation of tuft block 140 reached during different times or points in an oscillation cycle, as further described herein.

Referring to FIG. 4B, the next step in the method includes partially rotating the drive shaft using motor 170 (clockwise) through an angle of rotation less than 360 degrees which would represent one complete revolution of the drive shaft 130 and concomitantly one complete oscillation cycle of tuft block 140. During this initial partial shaft rotation, eccentric cam 139 begins to move clockwise about drive shaft 130. Through engagement of cam 139 with slot 141, the camming motion simultaneously begins to pivot or tilt tuft block 140 away from the vertical axis VA in a first lateral direction (i.e. left) such that vertical centerline VC is no longer axially aligned with vertical axis VA. The left lateral side 161 of intermediate portion 144 may translate laterally in position and come into contact with the left flange 147 which restricts the lateral displacement of tuft block 140 by cam 139.

Continuing rotation of the drive shaft 130 causes the tuft block 140 to further pivot and tilt laterally into a first fully tilted orientation "P1" shown in FIG. 4C facing outwards in a first lateral direction (i.e. to the left). Simultaneously, the tuft block 140 may move vertically upward slightly. A first tilt angle A2 is formed measured between vertical centerline VC and vertical axis VA. Angle A2 is less than 90 degrees and in some embodiments may be about 45 degrees or less. The degree to which tuft block 140 is tilted and angle A2 may be limited by contact between left side bottom surface 156 of upper bristle holding portion 142 and top surface 157 (e.g. rail 157a), and in some embodiments further or instead of by contact between one of the outwardly flared leg extensions 153 of base portion 143 (e.g. right side) with flange 147 or its respective concavely rounded shoulder 154 formed between the flange and wall 146b on the right side of tuft block 140 opposite the left flange engaging the bottom surface of the bristle holding portion and direction of tilt.

Further partial clockwise rotation of drive shaft 130 and eccentric cam 139 vertically raises the tuft block 140 towards the top vertical position "T" while at least partially or fully maintaining the first fully tilted orientation P1 during the translated vertical motion, as shown in FIG. 4D. During this rising motion, the right side outwardly flared leg extension 153 of base portion 143 maintains contact with and pivots about the right side flange 147 and/or the right shoulder 154 of toothbrush head portion 104. On the opposing side of tuft block 140, the left flange 147 slides downwards along curved lateral surface 155 on intermediate portion 144 (compare. FIGS. 4C and 4D).

Further partial clockwise rotation of the drive shaft 130 raises and pivots tuft block 140 back toward the vertical axis VA and into an upright orientation of the top vertical position "T" as shown in FIG. 4E. Top surface 159 of upper bristle holding portion 142 is returned to a position substantially perpendicular or 90 degrees (angle A1) to vertical VA such that the vertical centerline VC of tuft block 140 is axially aligned again and coincides with the vertical axis. Both outwardly flared leg extensions 153 of base portion 143 (right and left side) fully engage and contact their corresponding right and left flanges 147 and/or the shoulders 154 of toothbrush head portion 104 which limits the maximum vertical height reachable by the tuft block 140.

Figure 4F:
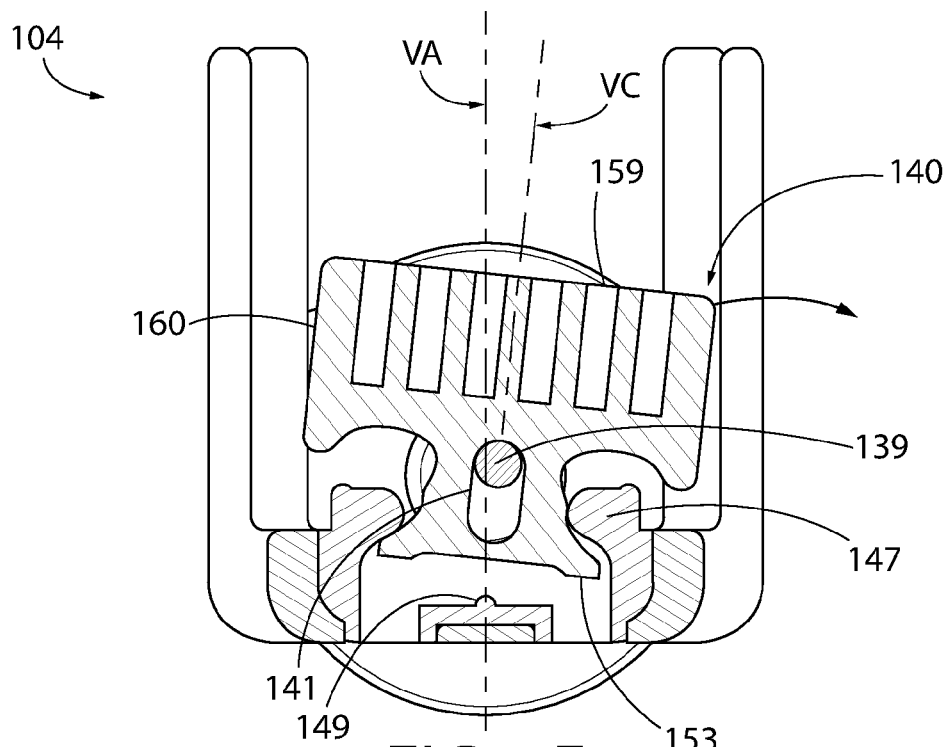

Referring to FIG. 4F, the method continues by partially rotating the drive shaft 130 producing a camming action in which cam 139 begins to pivot or tilt tuft block 140 away from the vertical axis VA in a second lateral direction (i.e. right) such that vertical centerline VC is no longer axially aligned once again with vertical axis VA. The right lateral side 161 of intermediate portion 144 may translate laterally in position and come into contact with the right flange 147 which restricts the lateral displacement of tuft block 140 by cam 139.

Figure 4G:
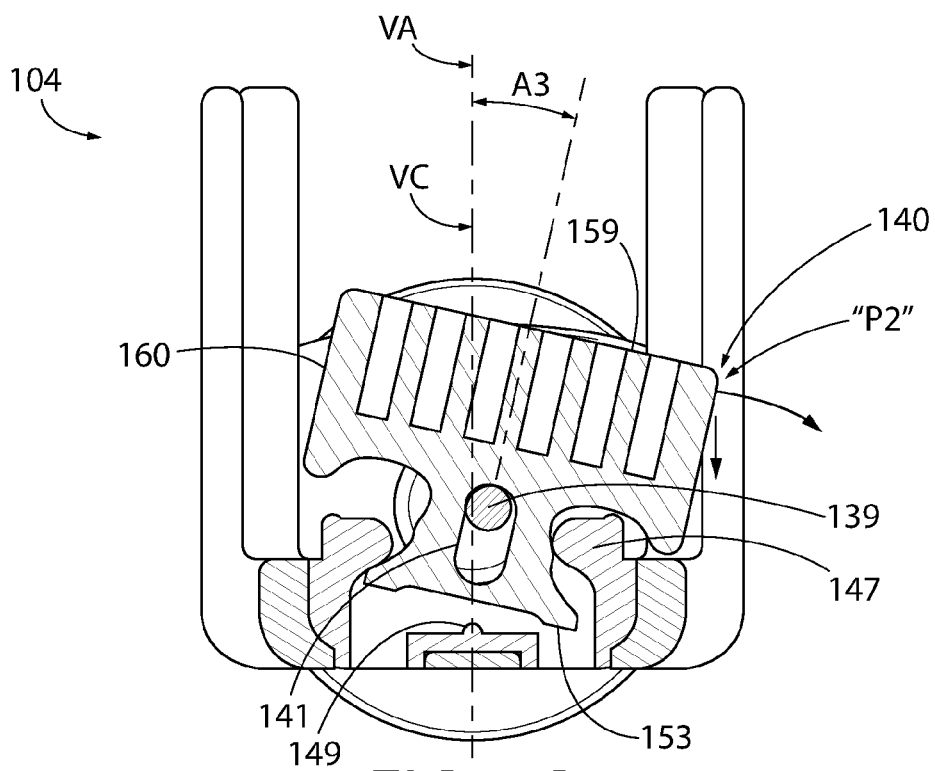

Continuing rotation of the drive shaft 130 causes the tuft block 140 to further pivot and tilt laterally into a second fully tilted orientation "P2" shown in FIG. 4G facing outwards in a second lateral direction (i.e. to the right). Simultaneously, the tuft block 140 may move vertically downward slightly. A second tilt angle A3 is formed measured between vertical centerline VC and vertical axis VA. Angle A3 is less than 90 degrees and in some embodiments may be about 45 degrees or less. In one embodiment, angle A3 may substantially equal to angle A2 of the first fully tilted position "P1" shown in FIG. 4C and described above. The degree to which tuft block 140 is tilted and angle A3 may be limited by contact between right side bottom surface 156 of upper bristle holding portion 142 and top surface 157 (e.g. rail 157b), and in some embodiments further or instead of by contact between one of the outwardly flared leg extensions 153 of base portion 143 (e.g. left side) with flange 147 or its respective concavely rounded shoulder 154 formed between the flange and wall 146a on the left side of tuft block 140 opposite the right flange engaging the bottom surface of the bristle holding portion and direction of tilt.

Further partial clockwise rotation of drive shaft 130 and eccentric cam 139 vertically lowers the tuft block 140 towards the bottom vertical position "B" while at least partially or fully maintaining the second fully tilted orientation P2 during the translated vertical motion, as shown in FIG. 4G. During this lowering motion, the left side outwardly flared leg extension 153 of base portion 143 maintains contact with and pivots about the left side flange 147 and/or the left shoulder 154 of toothbrush head portion 104. On the opposing side of tuft block 140, the right flange 147 slides downwards along curved lateral surface 155 on intermediate portion 144 (compare. FIGS. 4F and 4G).

Figure 4H:
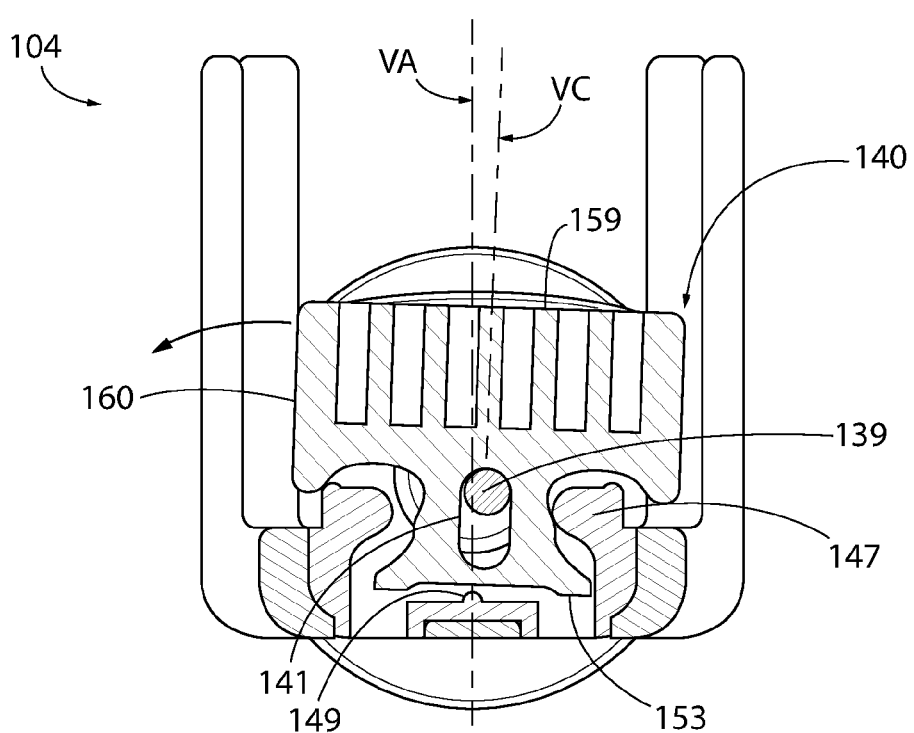

Further partial clockwise rotation of the drive shaft 130 as shown in FIG. 4H pivots and tilts the tuft block 140 back toward the vertical axis VA in the first lateral direction (i.e. left) and back towards bottom vertical position "B". During the action, contact may be broken between the left side outwardly flared leg extension 153 of base portion 143 the left side flange 147 and/or the left shoulder 154 of toothbrush head portion 104.

Figure 4I:
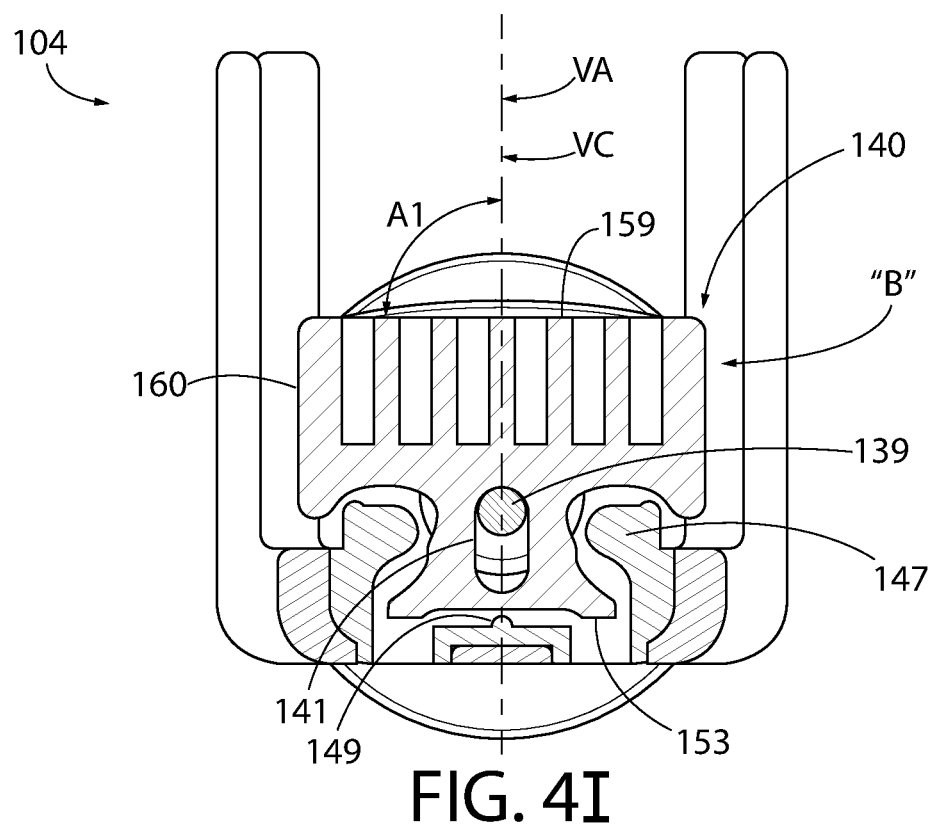

Referring to FIG. 4I, continuing partial clockwise rotation of drive shaft 130 returns tuft block 140 to the starting bottom vertical position "B" and an upright orientation as shown. This completes one oscillation cycle of tuft block 140 and a complete 360 degree revolution of drive shaft 130. The operation of toothbrush 100 and oscillating motions of tuft block 140 may continue by repeating the foregoing process steps.

Figure 5:
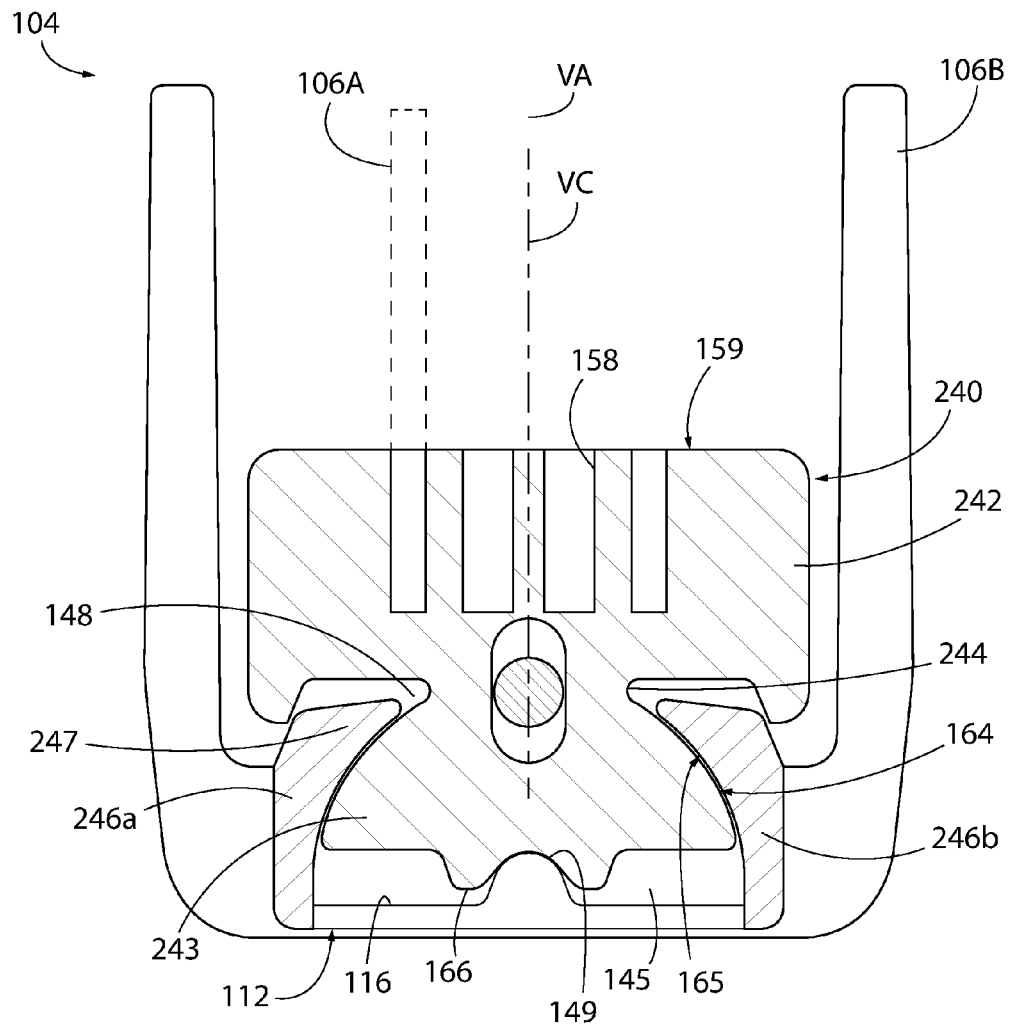
FIG. 5 is a transverse cross sectional view of an alternative embodiment of a movable tuft block.

FIG. 5 shows an alternative embodiment of toothbrush 100 in which tuft block 140 and head portion 104 are slightly reconfigured to provide lateral pivoting and tilting brushing motion only without vertical movement or displacement with respect to toothbrush head portion 104. In this configuration, tuft block 240 includes a base portion 243 having opposing convex arcuately curved bearing surfaces 164 configured for engaging complementary configured bearing surfaces 165 formed in receptacle 145 of toothbrush head portion 104. The concave arcuately curved bearing surfaces 165 may be formed on opposing receptacle walls 246a, 246b which further define opposing flanges 247 extending inwardly towards vertical axis VA. Flanges 247 are formed on a top portion of walls 246a, 246b and form a reduced width entrance 148 to receptacle 145 from front side 111 of toothbrush head 110 that precludes withdrawal of tuft block 240 through the front side.

The intermediate portion 244 of tuft block 240 may be severely truncated in height in contrast to intermediate portion 144 of tuft block 140 (see, e.g. FIG. 3) since this embodiment does not translate axially in a vertical direction. Base portion 243 defines a bottom surface 250 which engages pivot protuberance 149 in a similar manner to that already described for tuft block 140. In this embodiment, a pair of laterally spaced and downwardly extending ribs 166 may be provided between which protuberance 149 is received. Ribs 166 may be axially elongated in length along the longitudinal axis LA in toothbrush head portion 104 similarly to protuberance 149.

In operation, rotating drive shaft 130 oscillates tuft block 240 laterally sideways in opposing rocking or tilting motions and directions about central axis CA of the drive shaft via engagement of cam 139 with slot 141 in the tuft block. The vertical centerline VC of tuft block 240 will alternatingly be disposed at various angles to vertical axis VA of toothbrush head portion 104 during the oscillating motions. It should be noted that components not numbered in FIG. 5 are similar to the same components labeled in FIG. 3 unless specifically noted otherwise.

Figure 6A:
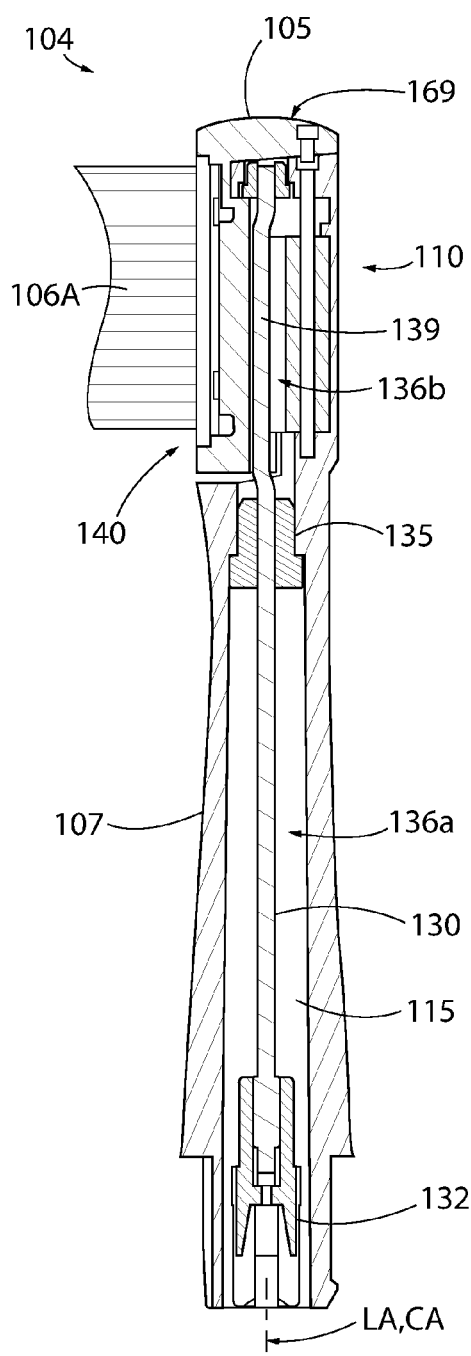
FIGS. 6A and 6B are side cross sectional and top plan views respectively of an alternative embodiment of a powered toothbrush head portion.
Figure 6B:
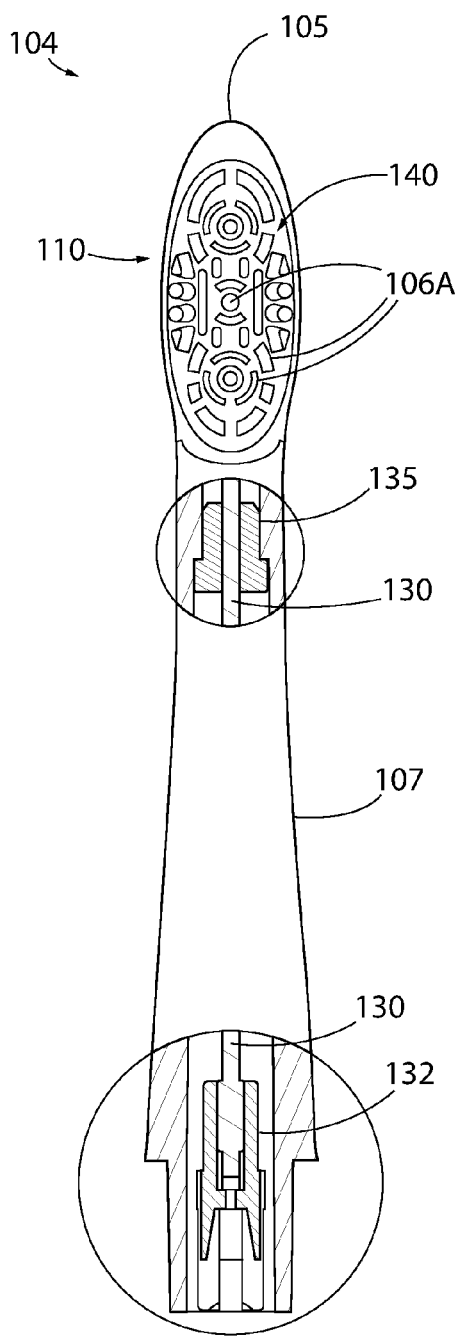

FIGS. 6A and 6B depict an alternative embodiment of toothbrush head portion 104 which includes a single oscillating tuft block 140. In this embodiment, tuft block has a generally oval shape (in top plan view) and is disposed near distal end 105 of toothbrush head 110. The tooth motor driven cleaning elements 106A comprise a plurality of bristles and elastomeric elements as shown. The tuft block 140 may be configured as shown in FIG. 3 for replicating Bass type brushing motions, or alternatively may be configured as shown in FIG. 5 for producing only lateral back and forth pivoting or tilting brushing action with respect to longitudinal axis LA.

Capacitive Touch Sensing Control

According to another aspect of the present invention, control panel 300 used to control the on/off operation and/or speed of the toothbrush 100 may include capacitive touch sensing technology in lieu of or in addition to mechanical switches.

Figure 8:
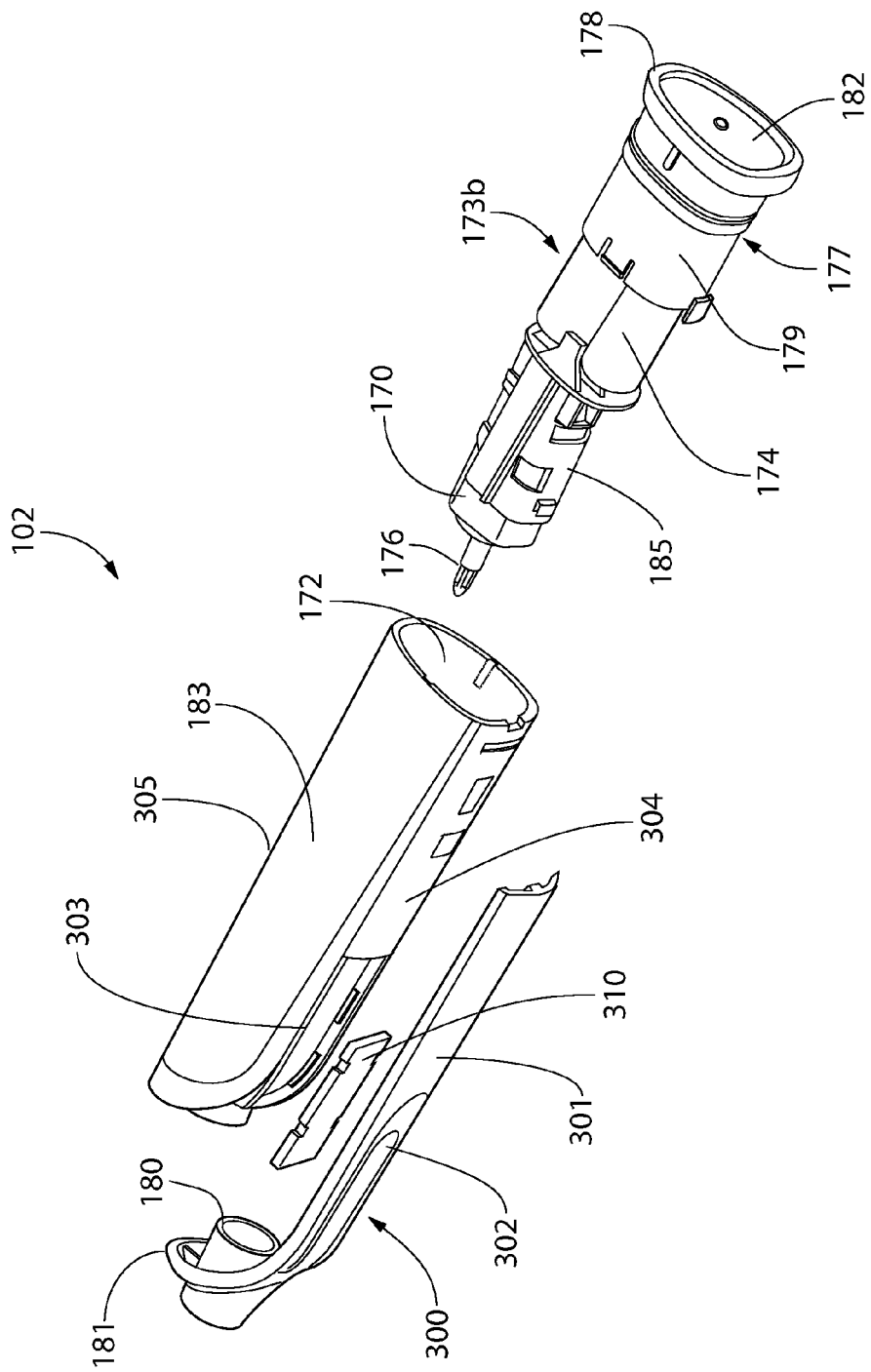
FIG. 8 is an exploded perspective view of another embodiment of a toothbrush including a handle portion incorporating a capacitive touch sensing control system.

FIG. 8 depicts an exploded perspective view of an exemplary embodiment of toothbrush 100 having a handle portion 102 which incorporates capacitive touch sensing technology. Features numbered similarly to FIGS. 1 and 7 are the same as previously described herein.

Referring to FIG. 8, the handle portion 102 may be constructed with a removable end cap assembly 177 providing a convenient access to battery compartment 173b for replaceable single use type batteries 174. End cap assembly 177 includes an end cap 178 which defines bottom wall 182 of handle portion 102 and tubular extension 179 configured for removably inserting and holding one or more batteries 174. In this embodiment, motor 170 may be mounted in a housing 185 which may be separate from or configured for attachment to end cap assembly 177. The motor housing 185 and end cap assembly 177 are insertable into downwardly open internal chamber 172 formed in handle portion 102. When mounted, end cap 178 closes the bottom of handle portion 102. Motor housing 185 and end cap assembly 177 may be retained in handle portion 102 by any suitable means known in the art.

Handle portion 102 includes a receptacle 303 configured for mounting a PCBA 310 (printed circuit board assembly) therein. Receptacle 303 opens through the front side 304 of handle portion 102 and communicates with internal chamber 172 to permit the passage and electrical connection of control wires from the PCBA 310 to the motor 170. PCBA 310 includes a capacitive touch sensor system, as further described herein.

With continuing reference to FIG. 8, front and rear portions of side walls 183 define a front side 304 and rear side 305. A detachable front face plate 301 may be provided in one embodiment which is configured for attachment to front side 304 by any suitable removable mechanical means (e.g. fasteners, snap fit, etc.) or non-removable mechanism means (e.g. adhesives, ultrasonic welding, etc.). In one embodiment, face plate 301 may be constructed to include front wall 181 of handle portion 102 and socket 180 which receives stem 184 of removable head portion 104 (see, e.g. FIGS. 2A and 2B). Front face plate 301 is configured to cover PCBA 310 and close the receptacle 303 when the face plate is mounted to the front side 304 of handle portion 102. Front face plate 301 may be formed of one or more materials. In one embodiment, front face plate may be formed of a suitable molded plastic material.

In one embodiment, front face plate 301 may include control panel 300. The control panel may be longitudinally elongated. Control panel 300 includes a thinned deformable actuation portion or panel 302 configured and structured to be elastically deformable and movable in response to applying an inward force F using light to moderate finger pressure. Actuation panel 302 functions to activate the capacitive touch sensor system for controlling operation of the toothbrush motor 170. Actuation panel 302 may be formed by a deformable section of front face plate 310 having a thickness selected to be sufficiently thin and elastically deformable in response to a finger touch pressure to activate the sensor system. In one embodiment, actuation panel 302 may have a reduced wall thickness in comparison to adjacent thicker and stiffer portions of front face plate 301 intended for grasping rather than control of the toothbrush 100.

The deformable actuation panel 302 may be formed integrally with face plate 301 as part of a single unitary structure of the face plate or alternatively may be a deformable insert which is permanently affixed along its peripheral edges to the face plate in a complementary configured opening. Either type of construction is suitable. In the latter construction, actuation panel 302 may be formed of a different material than the face plate 301. For example, in one possible embodiment in which face plate 301 is made of a substantially rigid plastic material, operating panel may be formed of either thin metal or thin plastic of a type different than the adjacent thicker portions of face plate 301 and therefore more readily deformable to serve its intended function. Portions of front face plate 301 over the actuation panel 302 may be covered by an elastomeric overlay material such as TPE in some embodiments.

The capacitive touch sensor system will now be described in further detail. In one embodiment, the capacitive touch sensor system may be a metal over capacitance (MOC) type system which works on the principal of providing a pair of spaced part and electrically isolated conductors forming a capacitor and measuring the change of capacitance with a microprocessor that occurs when the spacing between the conductors is changed by a finger touch and deflection of one of the conductors. Suitable microprocessor-based capacitive touch sensor system devices are commercially available from suppliers such as Microchip Technology, Inc. of Chandler, Ariz.

Figure 9:
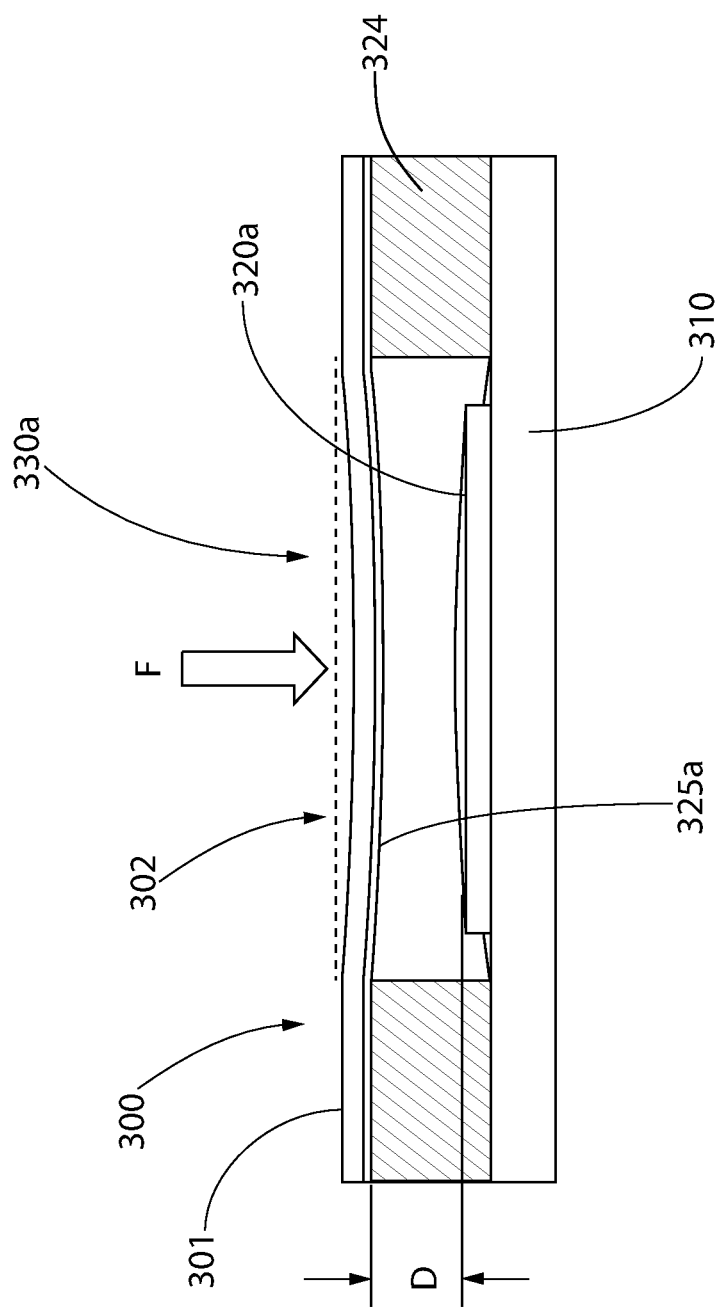
FIG. 9 is a side cross-sectional view of a capacitive touch sensor button including a pair of a movable sensor target and stationary capacitance sensor.
Figure 10:
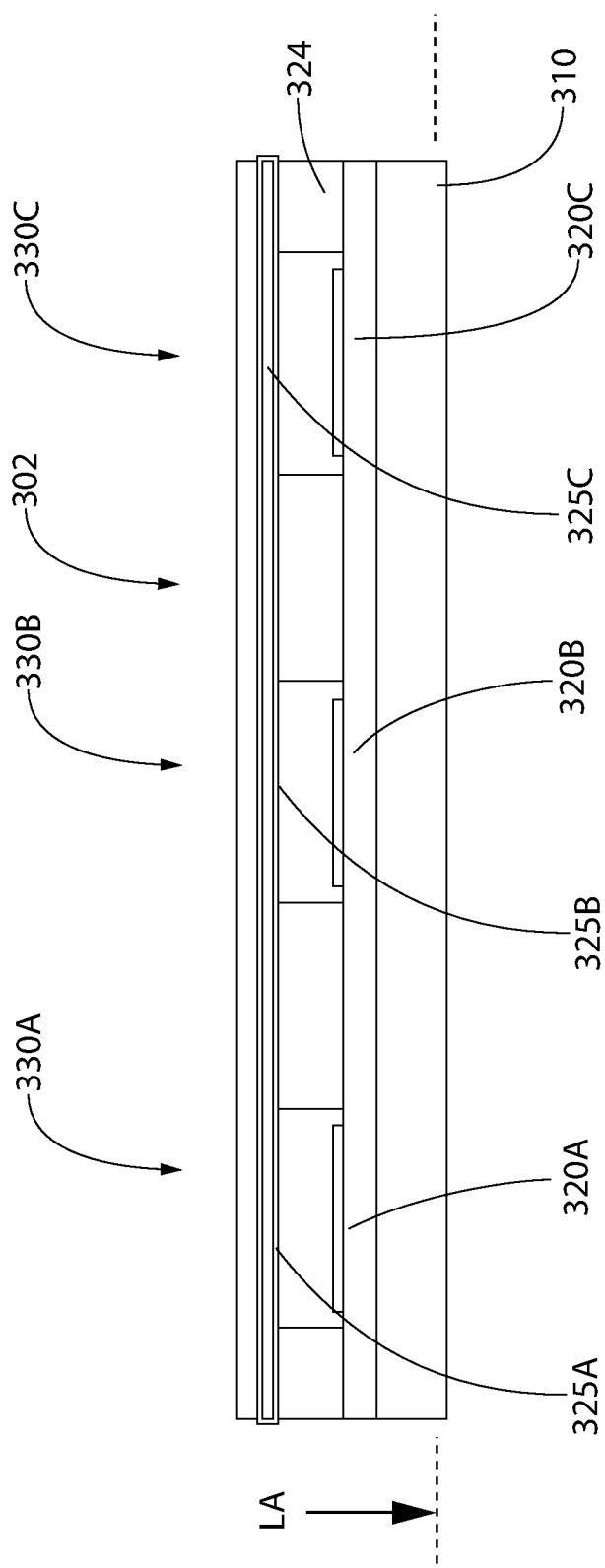
FIG. 10 is a side cross-sectional view of a linear array of the capacitive touch sensor buttons of FIG. 9.

Referring now to FIGS. 9 and 10, an MOC capacitive touch sensor system includes an array of sensor buttons 330a-c each comprised of a conductive capacitance sensor 320a-c and a corresponding transversely aligned conductive sensor target 325a-c spaced apart therefrom and separated by a distance D. In one embodiment, sensors 320a-c and sensor targets 325a-c may be formed of an electrically conductive metal; however, various other conductive materials including without limitation conductive semiconductor materials may be used. Sensors 320a-c may be mounted on PCBA 310 and are electrically connected to and energized by a power source such as battery 174 creating a capacitance. Sensors 320a-c remain stationary during operation of the control panel 300. By contrast, sensor targets 325a-c are movable during operation of the control panel transverse to longitudinal axis LA and attached to the underside of deformable operating panel 301. In one embodiment, sensor targets 325a-c may be formed by a thin metal film or layer affixed to the bottom (inner) surface of operating panel 301. The sensor buttons 330a-c are axially spaced apart along longitudinal axis LA and form electrically isolated discrete conductive elements which may be activated independently of each other by user touch.

Referring to FIGS. 9 and 10, spacer(s) 324 are provided between adjacent sensor buttons 330a-c which maintains physical separation (distance D) between sensors 320a-c and corresponding sensor targets 325a-c. The spacers 324 further isolate motion of each sensor button 330a-c from an adjacent button so that depressing a selected button and deflecting adjoining sensor target 325a-c via a finger touch to activate that sensor by changing distance D will not substantially change distance D in the adjacent unselected button which would render a false or errant unintended activation of the adjacent unselected button. Accordingly, the spacers 324 are preferably formed of a substantially rigid material to prevent deflection of the spacer during a finger touch/press action on actuation panel 302 and isolate the motion of each sensor button 330a-c so that the pressing force applied to one sensor button will not have a measurable effect on an adjacent button. Examples of suitable spacer materials are FR4 or non-deformable plastics. Adequate rigid mechanical support behind PCBA 310 is also preferably provided to prevent bending of PCBA substrate in the vicinity of sensors 320a-c to avoid loss of sensitivity. In some embodiments, spacers 324 may be formed by a continuous monolithic layer of spacer material with openings formed therein for each sensor button 330a-c or alternatively individual spacers. Either construction is acceptable; however, the former may be more cost effective.

Figure 11:
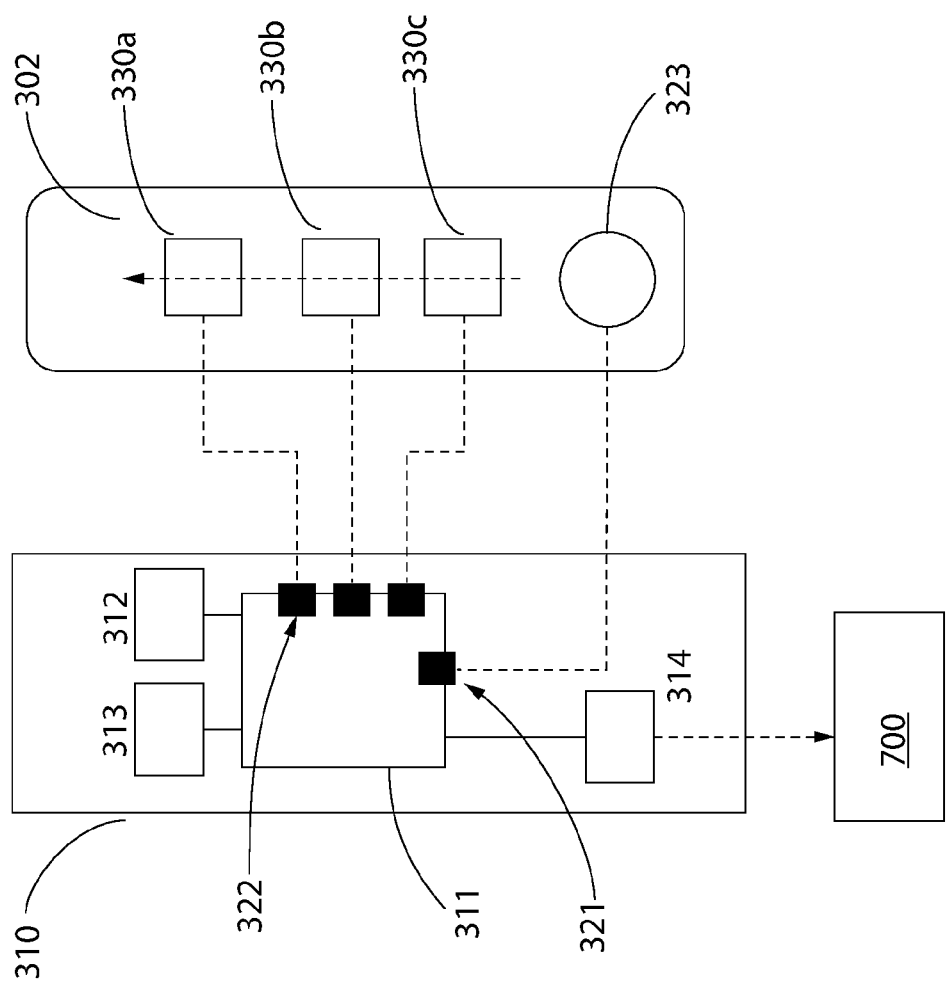
FIG. 11 is a schematic block diagram of the capacitive touch sensing control system.

In one exemplary embodiment, the array of sensor buttons 330a-c may include three sensor buttons arranged axially and linearly along the longitudinal axis LA of the toothbrush handle portion 102 which is illustrated in FIGS. 10 and 11. This arrangement is convenient for a powered toothbrush 100 which generally has a relatively narrow handle in width (transverse to the longitudinal axis LA) for ease of grasping. Other suitable numbers of sensor button 330a-c may be provided in other embodiments. The sensor button array is designed to detect specific user gestures and sense the application of pressure by a user to the deformable actuation panel 302 which are then translated by the software/firmware running on the microprocessor to control the functions of toothbrush 100 such as turning the product on/off and varying the motor speed and hence brushing action.

FIG. 11 is a schematic diagram of the actuation panel 302 and PCBA 310 of the capacitive touch sensor system. The system includes a programmable microprocessor 311 mounted on the PCBA 310 which is configured controls the operation of the toothbrush motor 170 and toothbrush 100 in conjunction with the sensor buttons 330a-c which provide a user input device for controlling the microprocessor. Microprocessor 311 is configured to recognize touch activation by a user of a sensor button 330a-c via sensors 320a-c and executes program instructions via firmware and/or software configured to direct the operation and control of toothbrush 100. In addition to microprocessor 311, the capacitive touch sensor system includes all other peripheral devices and components necessary to form a fully functional programmable data processing system as will be known to those skilled in the art. This may include without limitation suitable volatile and non-volatile memory 312 (e.g. RAM, ROM, etc.), timer 313 such as electronic and/or software timers, analog capacitance-to-digital converter, digital signal controllers, compensation circuitry, processor registers, peripheral interfaces, real time clock (RTC), non-transitory machine readable medium, circuits and data buses, input/output interfaces, drivers (e.g. display, LEDs, audio, etc.) and others. Batteries 174 may provide the power supply for microprocessor 311. Microprocessor 311 is configured and operable to convert the capacitance detected by sensors 320a-c into a digital value further manipulated by the microprocessor to direct operation of the toothbrush 100.

Sensitivity control is programmed into microprocessor 311 for touch detection in the form of a threshold capacitance value Ct to distinguish between an unintended soft touch on deformable actuation panel 302 and a harder touch intended to activate sensors 320a-c. This ensures that only a positive, intended harder touch is detected versus mere grasping and handling of the toothbrush 100 by a user. Accordingly, the microprocessor 311 may be programmed with a threshold capacitance detection value Ct which must be met or exceeded (correlated to the degree of deflection of the sensor target 325a-c by a user) before control of the toothbrush operation is implemented by the microprocessor.

Referring to FIG. 11, the sensors 320a-c associated with sensor buttons 330a-c are each connected to dedicated input ports 322 (e.g. pins, pads) on microprocessor 311 via conductive communication links (dashed lines) which transmits measured capacitance signals from each button to the microprocessor for detecting a user touch event. In one embodiment, an on/off switch 323 is provided which may be a capacitance touch sensor button similar to sensor buttons 330a-c or another digital switch which is operably linked to a separate input port 321 on the microprocessor 311 via a conductive communication link (dashed line). In other possible embodiments, the on/off switch may be a mechanical type switch which is not controlled by microprocessor 311 and instead is directly coupled electrically to the motor 170 via an electrical circuit for the toothbrush on/off operating function. In such an embodiment, the sensor buttons 330a-c may be used for controlling the speed of motor 170 after the toothbrush has been turned on.

Motor 170 may be a DC variable speed motor in which the MOC capacitive touch sensor system controls the rotational speed (RPM) of rotor 171 to vary the oscillation rate of the movable tuft blocks 120, 140. Variable speed operation may be accomplished by any suitable means used in art, including without limitation a motor speed controller 314 (see FIG. 11) such as an electronic speed controller (ESC) module or a pulse width modulator, both of which include appropriately configured electronic circuitry and devices (e.g. MOSFETs, oscillators, resistors, capacitors, etc.) configured to control the power supplied to motor 170 and hence its speed. Such DC motor speed control devices are commercially available. In one embodiment, these devices may be incorporated onto PCBA 310. The MOC capacitive touch sensor system is operably connected to and controls operation of the electronic speed controller.

Operation of the MOC capacitive touch sensor system will now be described. In one embodiment, the operation of microprocessor 311 may be configured via the program instructions or routines stored in memory 312 to provide a sliding mode of operation to control panel 302 (represented by dashed arrow in FIG. 11). In this embodiment, a linear array of sensor buttons 330a-c is provided in which the buttons (i.e. sensor 320a-c and sensor target 325a-c pairs) are arranged along the longitudinal axis LA of tooth brush 100. In this operating mode, the sensor system is programmed to recognize sequential sliding finger (or thumb) touching actions or gestures along control panel 300 across sensor buttons 330a-c for controlling the speed of motor 170 via motor speed controller 314. In the present embodiment to be described, control panel 300 includes three sensor buttons 300a-c. More or less capacitive touch sensor buttons may be used.

In one embodiment, microprocessor 311 may be programmed to require a sliding touching gesture across all three sensor buttons 330a-c in order to change the speed of motor 170 and oscillating speed of tuft blocks 120, 140. Using timer(s) 313, microprocessor 311 is programmed and configured to measure the actual time intervals T1-2 and T2-3 occurring between activation of each sensor buttons 330a-c by the user sliding their finger or thumb across the buttons. The time intervals may be measured in fractions of a second (e.g. tenths, hundredths, or thousandths) or in seconds in some embodiments. The actual time intervals T1-2 and T2-3 are compared by microprocessor 311 to a preprogrammed maximum time interval Tm stored in memory 312 for adjacent sensor button activation. The maximum time interval Tm represents the maximum permissible time lag between activation of adjacent sensor buttons 330a-c by a user that is allowed in order for the microprocessor to change the speed of motor 170, as further described herein. In this or other embodiments, microprocessor 311 may further be programmed to detect the sequential order in which the user activated the sensor buttons 330a-c for either increasing or decreasing the speed of motor 170.

If the time intervals T1-2 and T2-3 measured between sensor buttons 330a-b and 330b-c respectively are each less than or equal to maximum time interval Tm, the motor speed controller 314 is activated to change speed of motor 170 (i.e. increase or decrease) from a first speed to a second speed (RPM). In one possible embodiment, selecting the sensor buttons in a first sequential order of 330a-330b-330c (representing a sliding finger gesture with sufficient inward force F in a first longitudinal direction) increases the motor speed, and selecting the buttons in a second sequential order of 330c-330b-330a (representing a sliding finger gesture with sufficient inward force F in a second opposite longitudinal direction) decreases motor speed.

In some embodiments, motor 170 may be operated in incrementally increasing or decreasing speeds S1, S2, S3 . . . Sn (where Sn=the maximum number of motor speeds programmed into microprocessor 311) corresponding to successive finger touching slides or swipes across control panel 300 and sensor buttons 330a-c therein. Accordingly, the speed of motor 170 and concomitantly oscillating speed of movable tuft blocks 120, 140 may be incrementally increased or decreased to suit a user's preferences by successive swiping actions across the control panel in the first or second longitudinal directions between the minimum speed S1 and maximum speed Sn).

If one of the measured time intervals T1-2 or T2-3 sensed by microprocessor 311 is greater than time interval Tm, the motor speed controller 314 is not activated by the microprocessor 311 and the speed of motor 170 is not changed. This prevents inadvertent sliding touching gestures across control panel 300 typically occurring over a greater period of time such as during routine handling of the toothbrush 100 from changing motor speed which is thereby distinguished from intentional and more rapid speed-changing gestures by a user.

Microprocessor 311 may be configured to change the speed S1 . . . Sn of toothbrush motor 170 by one increment in a step-like fashion (e.g. 800 RPM at S3 to 900 RPM at S4 or 900 at S4 to 800 RPM at S3) each time a valid user finger slide is recognized across deformable actuation panel 302 which activates sensor buttons 330a-c. Any suitable incremental change in speed may be used and pre-programmed into microprocessor 311 between each speed S1 . . . Sn. Furthermore, any suitable number of speeds S1 to Sn may be used and programmed into microprocessor 311.

In another configuration, the microprocessor 311 may be configured to recognize fast finger or thumb swipes across deformable actuation panel 302 and correspondingly be programmed to skip speed increments during a motor speed change gesture. Advantageously, this allows a user to increase or the speed of the toothbrush (depending on the sequential order of sensor button 330a-c activation or linear swiping direction) from a first amount to a second amount in larger increments more quickly. For example, a faster finger or thumb swiping or sliding pressing action or gesture on deformable actuation panel 302 may increase motor speed by two or more increments per fast swipe (e.g. lower speed S1 to higher speeds S3 or S4, higher speed S4 to lower speeds S1 or S2, etc.). To implement this functionality in one non-limiting embodiment, the microprocessor 311 may be preprogrammed with a secondary time interval Tm2 which is less than maximum time interval Tm. Accordingly, in one example, if the time intervals T1-2 and T2-3 measured between sensor buttons 330a-b and 330b-c respectively are each less than or equal to maximum time interval Tm, the motor speed controller 314 is activated to change speed of motor 170 (i.e. increase or decrease) from a first speed to a second speed (RPM), as described above. This is a threshold condition for initiating a change in the speed of the motor in the first instance. The microprocessor 311 then makes an additional determination whether the time intervals T1-2 and T2-3 are each less than or equal to the secondary time interval Tm2. If this additional condition is met, microprocessor 311 will change the motor speed by multiple increments between S1 . . . Sn rather than a single increment. The number of increments to skip for each "fast swipe" speed change may be preprogrammed into the microprocessor. Using this same methodology, additional even faster swipe speed changes may be programmed into microprocessor 311 based on a tertiary time interval Tm3 which is less than Tm2.

Figure 12:
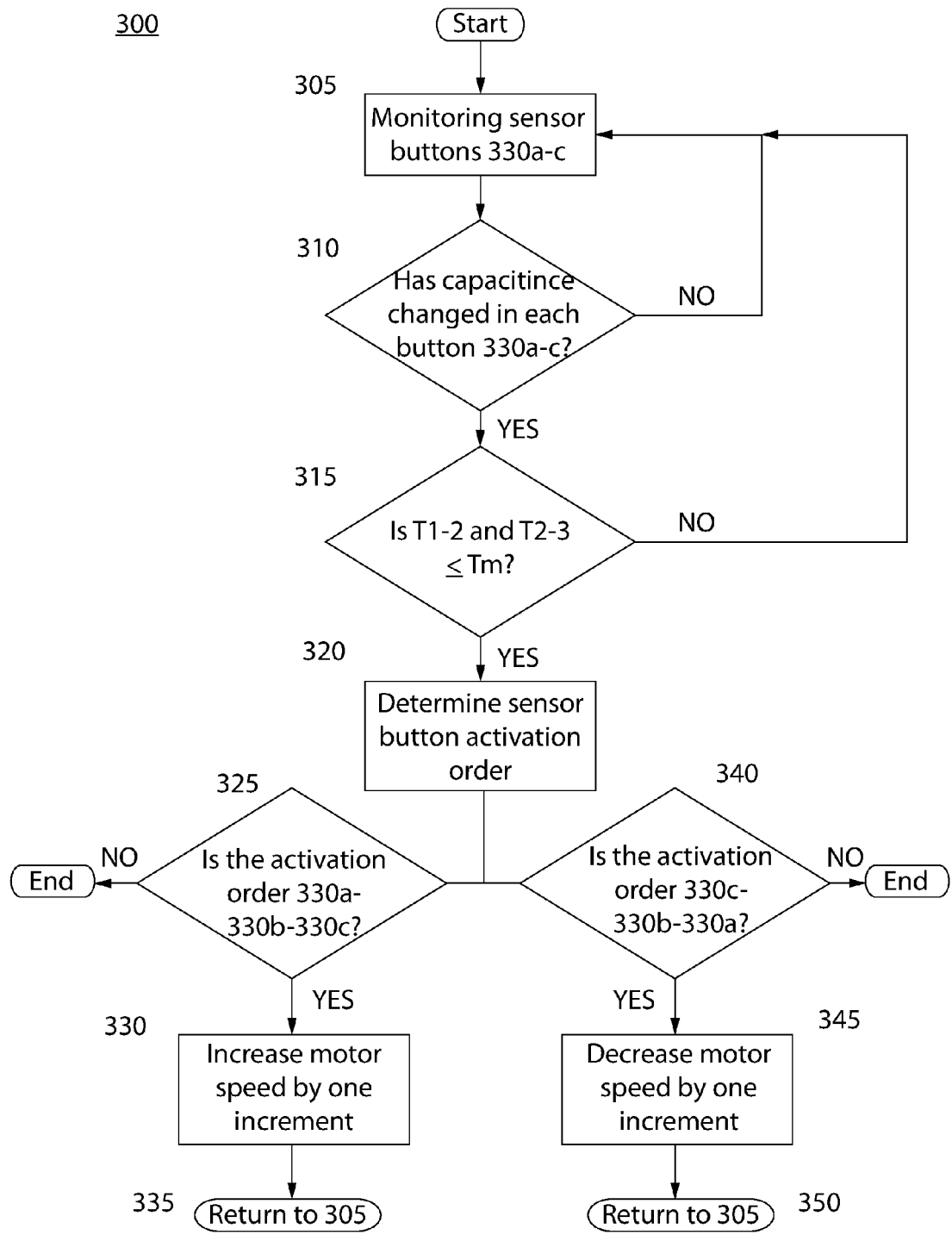
FIG. 12 is a flow chart of an exemplary process for controlling the speed of the toothbrush.

FIG. 12 depicts one exemplary process 300 of the MOC capacitive touch sensor system for controlling operation of a powered toothbrush using the foregoing microprocessor programming for sequential activation of sensor buttons 330a-c via sliding touching gestures by a user. The steps shown are performed by microprocessor 311 executing program instructions in response to sliding finger or thumb touches or gestures by a user across control panel 300 which activate sensor buttons 330a-c and motor speed control.

Referring now to FIG. 12, process 300 begins with a user sliding their finger or thumb across the deformable actuation panel 302 of toothbrush head portion 102 with sufficient inward pressing force F to activate sensor buttons 330a-c. The sensor targets 325a-c are pressed downwards towards sensors 320a-c as the actuation panel 302 of control panel 300 flexes and thereby increases the capacitance in each of the sensor button locations which is detectable by microprocessor 311 indicating a touching action has been sensed. In step 305, the microprocessor 311 of the MOC capacitive touch sensor system continuously monitors sensor buttons 330a-c when toothbrush 100 is turned on for a capacitance change. In step 310, if a capacitance change is not detected, the monitoring process continued. If a capacitance change is detected in each sensor buttons 330a-c, control passes to step 315 for a decision. The microprocessor 311 compares actual time intervals T1-2 and T2-3 to determine whether or not each of those times are less than or equal to the maximum time interval Tm. If T1-2 or T2-3 is greater than Tm, a false result occurs ("No") indicating an unintended activation of the sensor buttons 330a-c. Control returns to monitoring the sensor buttons 330a-c in step 305 for occurrence of another touching event.

If in step 315 each measured actual time intervals T1-2 and T2-3 is less than or equal to Tm, a true result occurs ("Yes") indicating that the user intended to increase or decrease the speed of toothbrush motor 170 by one increment. Control passes to step 320. It should be noted that in some alternative embodiments with the fast swipe speed change feature already described herein, the microprocessor 311 may be programmed to make an additional determination whether the time intervals T1-2 and T2-3 are each less than or equal to the secondary time interval Tm2 in addition to being less than maximum time interval Tm. If this additional condition is met, microprocessor 311 will change the motor speed by multiple increments between S1 . . . Sn rather than a single increment.

In step 320, the microprocessor 311 determines the order in which the user activated the sensor buttons 330a-c. If the sequential activation order is 330a-330b-330c in step 325, the microprocessor 311 sends a control signal to motor speed controller 314 to increase the speed of the toothbrush motor 170 by one increment in step 330. In step 350, control is returned to monitoring the sensor buttons 330a-c in step 305 for occurrence of another touching event. On the other hand, if the sequential activation order is 330c-330b-330a in step 340, the microprocessor 311 sends a control signal to motor speed controller 314 to decrease the speed of the toothbrush motor 170 by one increment in step 345. In step 350, control is returned to monitoring the sensor buttons 330a-c in step 305 for occurrence of another touching event.

Although the foregoing embodiment describes changing the speed of toothbrush motor 170 may one increment in speed S1 . . . Sn each time a valid slide action is detected by the control panel 300, it will be appreciated that microprocessor 311 be programmed in some embodiments to change speed by two or more increments depending on the actual time intervals T1-2 and T2-3 measured by the MOC capacitive touch sensor system. For example, a valid slow finger swipe across deformable actuation panel 302 which at least meets or exceeds maximum time interval Tm up to a first time interval Ts1 may increase or decrease the speed by a single increment. A valid faster finger swipe across the actuation panel 302 which exceeds the first time interval Ts1 may increase or decrease the speed by two increments. If many speed level options are provided with toothbrush 100, this arrangement allows a user to skip through speeds more quickly to reach a desired level.

It will be appreciated that numerous variations are possible for controlling the motor speed of toothbrush 100 using the present sliding-type capacitive touch sensor system which is responsive to sliding finger pressure gestures of a user. Accordingly, the invention is not limited to the non-restrictive examples provided herein used to illustrate the operation of the MOC capacitive touch sensor system.

It will further be appreciated that the exposed outer surface of control panel 300 may or may not include indicia or markings indicating the locations of the sensor buttons 330a-c beneath the deformable capacitive touch actuation panel 302 to a user. Accordingly, the actuation panel 302 may be plain or unmarked in some embodiments. Either of the foregoing approaches to marking may therefore be used with the present invention.

Figure 13:
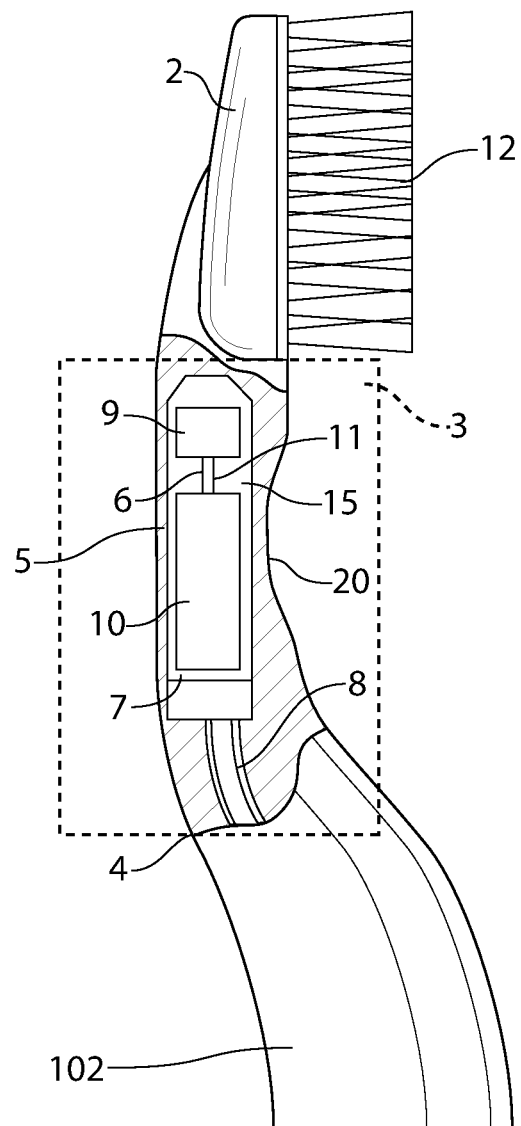
FIG. 13 is a side cross-sectional view of a head and neck portion of a vibrating sonic type toothbrush having a head to which vibrations are imparted, and incorporating a capacitive touch sensing control system.

FIG. 13 shows an exemplary embodiment of a vibrating sonic type toothbrush which may also be controlled using the MOC capacitive touch sensor system described herein. Such toothbrushes are described in U.S. Pat. No. 7,886,393, which is incorporated herein by reference in its entirety. The vibrating toothbrush of FIG. 12 generally comprises a handle which may be handle portion 102 containing the capacitive touch sensor system, a cleaning head 2 usually having cleaning elements 12, and a neck 3 disposed between the head 2 and the handle 1. While the cleaning head 2 illustrates bristles 12, other cleaning elements of various size, cross-section, material, etc., such as rubber elements, elastomeric elements, polishing elements, abrasive elements, floss-like cleaning elements, etc., may be used. The head 2 and neck 3 are usually formed of a relatively stiff material, such as polypropylene (PP), although other materials may be used. However, such material is also relatively elastic such that the neck and head can vibrate during use.

The neck 3 contains a mechanical vibratory device 5 that preferably includes a motor 10 and a vibratory element such as an eccentric weight 9 connected thereto by a shaft 11. By methods well known in the art, the vibratory device 5 can be connected to a power source such as an electrical power source such as battery 174 disposed in handle portion 102 via electrical connections 8 provided in the neck 3, and activated by deformable actuation panel 302 which includes the user touchable capacitive sensor buttons 330a-c (see also FIGS. 7-11). Alternatively, the power source can be located outside of the toothbrush, such as with direct current via a wall socket connection. In addition, the neck 3 can be formed as a unitary structure with the head 2 and handle 1 such as by injection molding or the like, or it can be separable from the handle 1 (not shown) preferably along location 4.

The mechanical vibratory device 5 produces vibrations in the head 2 through rotation of the eccentric weight 9 about the shaft 11. The motor 10 and eccentric weight 9 are preferably accommodated in a structural housing 15, which is preferably positioned in the neck 3 adjacent the head 2. The vibrations produced occur nearest the eccentric weight 9, which is positioned closer to the head 2 than the motor 10, which is closer to the handle 1 than the head 2. As noted above, the neck 3 is preferably made of an elastic material which facilitates the transmission of the vibrations from the weight 9 to the head 2. Of course, the mechanical vibratory device 5 can be positioned in a location that is not adjacent the head 2 as shown, as long as there are means to transmit the generated vibrations to the head 2.

Figure 14:
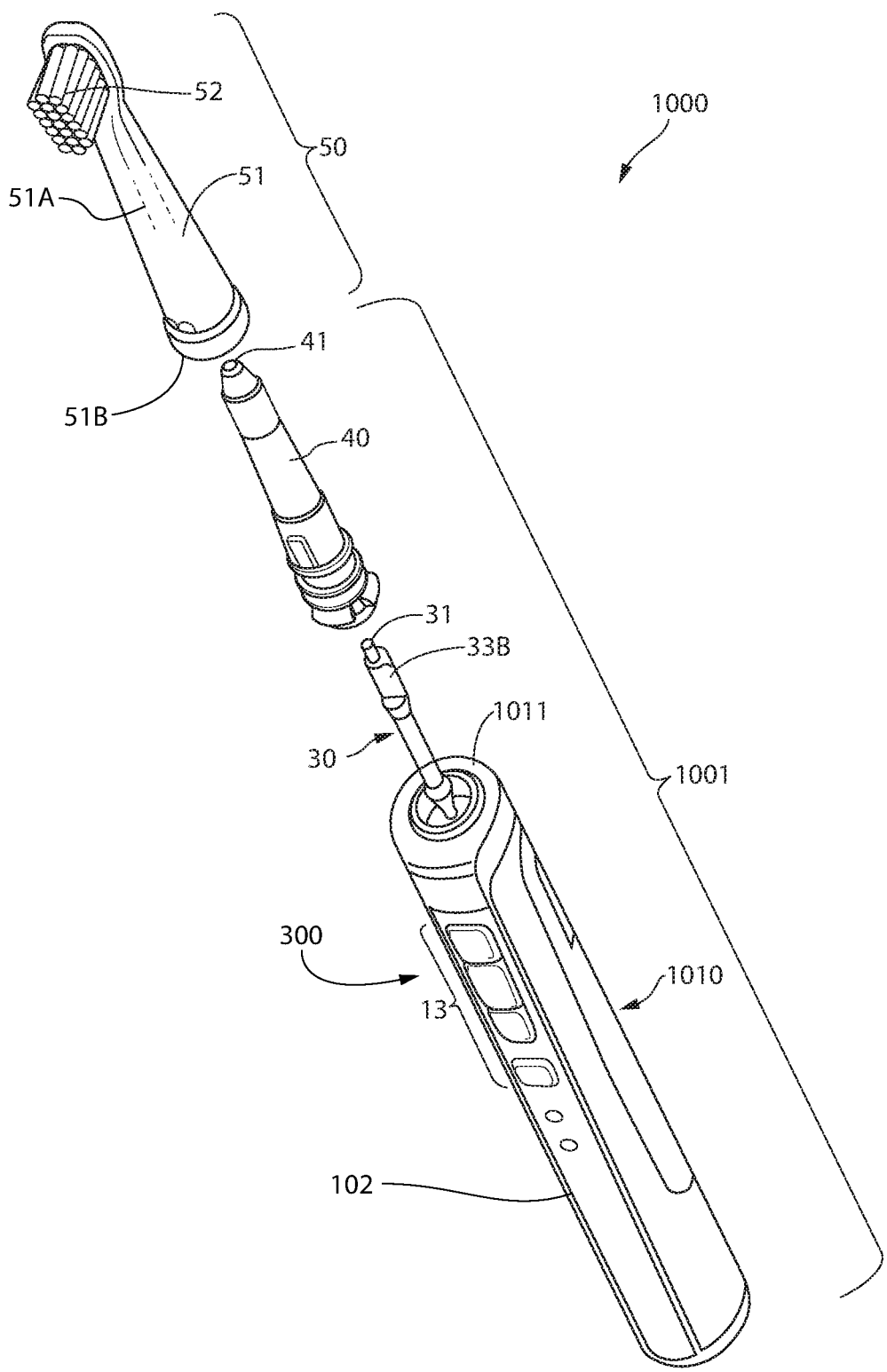
FIG. 14 is a perspective view of a vibrating sonic type toothbrush having a replaceable heads, and incorporating a capacitive touch sensing control system.

FIG. 14 shows an exemplary embodiment of a vibrating sonic type toothbrush having replaceable heads which may also be controlled using the MOC capacitive touch sensor system described herein. Such toothbrushes are described in PCT International Patent Application No. PCT/US2012/042973 filed Jun. 18, 2012, which is incorporated herein by reference in its entirety. The vibrating toothbrush of FIG. 11 generally comprises a handle which may be handle portion 102 containing the capacitive touch sensor system. Electric toothbrush 1000 includes an electric toothbrush main body 1001 and a replacement brush 50. Electric toothbrush main body 1001 includes a case 1010 forming toothbrush handle portion 102, a motor 20, an eccentric rod 30, and a stem 40 having such a form as to extend along a center axis 30t. Case 10 is formed in a tube shape. Case 10 is grasped by a user of electric toothbrush 100. Case 10 has a surface on which a control part 13 such as control panel 300 may be provided.

Motor 20 is incorporated near a first end 1011 of case 1010. Motor 20 has a driving shaft 21. Motor 20 is connected to a predetermined power supply (not shown) incorporated in case 1010, in order to rotate driving shaft 21. Eccentric rod 30 is formed in an almost bar shape. Eccentric rod 30 has a weight part 33b. Weight part 33b has a barycenter position which is displaced outward from center axis 30t of eccentric rod 30 (downward in FIG. 9). In other words, weight part 33b is eccentric with respect to center axis 30t of eccentric rod 30. Eccentric rod 30 has a second end 32 side connected to driving shaft 21.

Stem 40 has a cylinder shape (a cap shape). Stem 40 has a first end 41 side which is closed, and a bearing part 44 (not shown) is provided inside the first end 41 side. Eccentric rod 30 has a first end 31 which is inserted into bearing part 44. Stem 40 is attached to the case 1010 side so as to cover eccentric rod 30. Cylinder-shaped leading end part 41 of stem 40 is smaller in diameter than the other region of stem 40. Replacement brush 50 has a tubular part 51 which has an open trailing end 51b, a holding part 51a which is formed inside a leading end side of tubular part 51 and holds leading end part 41 of stem 40, and a brush part 52 which is provided outside the leading end side of tubular part 51. Tubular part 51 of replacement brush 50 is attached outside stem 40 so as to cover stem 40.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention.

Thus, the spirit and scope of the invention should be construed broadly as set forth in the appended claims.

What is claimed is:

1. A powered toothbrush apparatus with capacitive touch control, the toothbrush apparatus comprising:
   a motor;
   a handle portion;
   a capacitive touch control panel in the handle portion;
   a plurality of capacitance sensors operably associated with the control panel, each of the plurality of capacitance sensors having a capacitance value that is changed by a user touching a specific location of the control panel, thereby activating the capacitance sensor;
   a microprocessor in the handle portion, the microprocessor electrically connected to the plurality of capacitance sensors and the motor, the microprocessor configured to: (1) detect changes in the capacitance values of the plurality of capacitance sensors; (2) measure time intervals occurring between changes in the capacitance values of adjacent ones of the plurality of capacitance sensors; and (3) change speed of the motor upon determining that each of the plurality of capacitance sensors has been activated in a predetermined sequential order and that each of the measured time intervals is at or below a maximum predetermined time interval.

2. The toothbrush apparatus of claim 1, wherein the speed of the motor is not changed when the microprocessor detects that any one of the measured time intervals is greater than the maximum predetermined time interval preprogrammed into the microprocessor.

3. The toothbrush apparatus of claim 1, wherein the microprocessor is further configured and operable to change speed of the motor by a first amount upon determining that each of the measured time intervals is at or below the maximum predetermined value, and change speed of the motor by a second different amount upon determining that each of the values is below a second predetermined time interval programmed into the microprocessor, the second predetermined time interval being less than the maximum predetermined time interval.

4. The toothbrush apparatus of claim 1, wherein each sensor is arranged in a pair with a corresponding conductive sensor target separated from the sensor by a distance and supported by a deformable actuation portion of control panel which is deformable by the application of finger pressure by the user, wherein changing the distance between the sensor and sensor target by applying finger pressure to the deformable actuation portion changes the capacitance associated with the sensor and sensor target pair.

5. The toothbrush apparatus of claim 4, wherein a user sliding a finger across the sensor targets are positioned and arranged such that a user applying an inward touching force on the deformable actuation portion of the control panel adjacent one of the sensor targets changes the distance between that sensor target and its paired sensor thereby changing the capacitance of the sensor and sensor target pair detected by the microprocessor.

6. The toothbrush apparatus of claim 4, wherein the sensor targets are formed by a sheet or film of conductive metal applied to the underside of the deformable actuation portion of the control panel.

7. The toothbrush apparatus of claim 4, wherein the sensors are mounted on a printed circuit board in axially spaced apart relationship, the circuit board located below the control panel.

8. The toothbrush apparatus of claim 4, further comprising a spacer disposed adjacent each sensor and sensor target pair that maintains the distance between each paired sensor and sensor target.

9. The toothbrush apparatus brush of claim 8, wherein the spacer is formed of a rigid material which is not deformable by application of finger pressure.

10. The toothbrush apparatus of claim 4, wherein three pairs of sensor targets and sensors are provided and axially spaced apart along the longitudinal axis in control panel.

11. A powered toothbrush apparatus with capacitive touch control, the toothbrush comprising:
    a motor;
    a handle portion;
    a capacitive touch control panel mounted in the handle portion, the control panel being elastically deformable in response to the application of inward directed finger pressure by a user;
    a plurality of capacitance sensors mounted in the handle portion, each sensor paired with a corresponding movable conductive sensor target disposed on the deformable control panel above the sensor, each sensor target being movable towards its paired sensor in response to a user applying finger pressure to the control panel, wherein each sensor and sensor target pair has a capacitance that is changed by applying finger pressure on the control panel adjacent to the sensor target;
    a microprocessor mounted in the handle portion and electrically connected to the sensors and the motor, the microprocessor being configured to:
    detect changes in the capacitance values of the plurality of capacitance sensors;
    measure time intervals occurring between changes in the capacitance values of adjacent ones of the plurality of capacitance sensors; and
    change speed of the motor upon determining that each of the plurality of capacitance sensors has been activated in a predetermined sequential order and that each of the measured time intervals is at or below a maximum predetermined time interval.

12. The toothbrush apparatus of claim 11, wherein the microprocessor is further configured and operable to change speed of the motor by a first amount upon determining that each of the measured time intervals is at or below the maximum predetermined value, and change speed of the motor by a second different amount upon determining that each of the values is below a second predetermined time interval programmed into the microprocessor, the second predetermined time interval being less than the maximum predetermined time interval.

* * * * *